(12) United States Patent
Darwood

(10) Patent No.: US 10,251,723 B2
(45) Date of Patent: Apr. 9, 2019

(54) METHOD AND APPARATUS FOR USE IN THE PRODUCTION OF A SURGICAL GUIDE

(71) Applicant: Prometheus Surgical Limited, London (GB)

(72) Inventor: Alastair Darwood, London (GB)

(73) Assignee: Prometheus Surgical Limited, London (GB)

( * ) Notice: Subject to any disclaimer, the term of this patent is extended or adjusted under 35 U.S.C. 154(b) by 342 days.

(21) Appl. No.: 15/164,361

(22) Filed: May 25, 2016

(65) Prior Publication Data
US 2016/0342766 A1 Nov. 24, 2016

Related U.S. Application Data

(63) Continuation of application No. PCT/GB2014/053304, filed on Nov. 5, 2014.

(30) Foreign Application Priority Data

Nov. 25, 2013 (GB) .................................. 1320745.1

(51) Int. Cl.
*G06F 19/00* (2018.01)
*A61B 17/17* (2006.01)
(Continued)

(52) U.S. Cl.
CPC .............. *A61B 90/36* (2016.02); *A61B 17/17* (2013.01); *A61B 17/1739* (2013.01);
(Continued)

(58) Field of Classification Search
None
See application file for complete search history.

(56) References Cited

U.S. PATENT DOCUMENTS

| 5,027,281 A | 6/1991 | Rekow et al. |
| 5,338,198 A | 8/1994 | Wu et al. |

(Continued)

FOREIGN PATENT DOCUMENTS

| AU | 2014200073 A1 | 12/2013 |
| BE | 1018900 AF | 7/2012 |

(Continued)

OTHER PUBLICATIONS

Search Report dated May 14, 2014 in connection with the British Patent Application GB1320745.1.

(Continued)

*Primary Examiner* — Ramesh B Patel
(74) *Attorney, Agent, or Firm* — Corridor Law Group, P.C.

(57) ABSTRACT

A method of producing a modification plan for producing a surgical guide from an impression element includes: obtaining surface data representing a configuration of a surface of an impression element providing an impression of a surgical site; obtaining image data of a patient's anatomy; obtaining surgical plan data providing a surgical plan with respect to features in the image data representing anatomical features of the patient's anatomy; registering the impression element using the surface data and the image data with anatomical features of the patient's anatomy; and producing a modification plan from the surgical plan data using the registration of the impression element with anatomical features of the patient's anatomy, the modification plan being a plan for modifying the impression element.

20 Claims, 17 Drawing Sheets

(51) Int. Cl.
  *A61B 34/10* (2016.01)
  *A61B 90/00* (2016.01)
  *G16H 50/50* (2018.01)
  *A61B 17/00* (2006.01)
  *A61B 17/56* (2006.01)

(52) U.S. Cl.
  CPC .......... *A61B 17/1778* (2016.11); *A61B 34/10* (2016.02); *G06F 19/00* (2013.01); *G16H 50/50* (2018.01); *A61B 2017/00526* (2013.01); *A61B 2017/00946* (2013.01); *A61B 2017/00955* (2013.01); *A61B 2017/568* (2013.01); *A61B 2034/105* (2016.02); *A61B 2034/108* (2016.02); *A61B 2090/363* (2016.02)

(56) References Cited

U.S. PATENT DOCUMENTS

| | | | |
|---|---|---|---|
| 7,833,269 | B2 | 11/2010 | Nycz et al. |
| 8,092,543 | B2 | 1/2012 | Nycz et al. |
| 8,702,686 | B2 | 4/2014 | Geebelen et al. |
| 2004/0243146 | A1 | 12/2004 | Chesbrough et al. |
| 2007/0172506 | A1 | 6/2007 | Nycz et al. |
| 2008/0026338 | A1* | 1/2008 | Cinader .................. A61C 1/084 433/29 |
| 2008/0085489 | A1* | 4/2008 | Schmitt .................. A61C 1/084 433/75 |
| 2008/0114368 | A1 | 5/2008 | Shimko et al. |
| 2008/0287954 | A1* | 11/2008 | Kunz .................... A61B 17/175 606/87 |
| 2009/0163923 | A1 | 6/2009 | Flett et al. |
| 2010/0023015 | A1 | 1/2010 | Park |
| 2010/0151417 | A1* | 6/2010 | Nilsson .................. A61C 7/002 433/167 |
| 2011/0008751 | A1 | 1/2011 | Pettersson |
| 2011/0035025 | A1 | 2/2011 | Nycz et al. |
| 2011/0066267 | A1 | 3/2011 | Schmitt |
| 2011/0087332 | A1* | 4/2011 | Bojarski .............. A61B 17/155 623/20.32 |
| 2011/0093023 | A1* | 4/2011 | Lee ...................... A61B 17/175 606/86 R |
| 2012/0123576 | A1* | 5/2012 | Pettersson .............. G16H 50/50 700/98 |
| 2012/0179147 | A1 | 6/2012 | Geebelen |
| 2012/0230567 | A1 | 9/2012 | Greenberg |
| 2013/0081247 | A1* | 4/2013 | Fitz ...................... A61B 5/4528 29/407.09 |
| 2013/0119579 | A1 | 5/2013 | Iannotti et al. |
| 2013/0211531 | A1* | 8/2013 | Steines ................. A61F 2/4684 623/20.35 |
| 2013/0236874 | A1 | 9/2013 | Iannotti et al. |
| 2014/0074099 | A1* | 3/2014 | Vigneron ............... A61B 17/15 606/87 |
| 2014/0228860 | A1* | 8/2014 | Steines ............... A61F 2/30942 606/130 |
| 2014/0257508 | A1* | 9/2014 | Bojarski ............... A61F 2/3859 623/20.35 |

FOREIGN PATENT DOCUMENTS

| | | |
|---|---|---|
| CN | 101578076 A | 11/2009 |
| CN | 101711695 A | 5/2010 |
| CN | 102933163 A | 2/2013 |
| EP | 2168507 A2 | 3/2010 |
| EP | 2228029 A2 | 9/2010 |
| EP | 2475311 A1 | 7/2012 |
| EP | 2649951 A3 | 10/2013 |
| EP | 2671520 A3 | 12/2013 |
| EP | 2671521 A3 | 12/2013 |
| EP | 2671522 A3 | 12/2013 |
| EP | 2710967 A2 | 3/2014 |
| JP | H222010526605 A | 8/2010 |
| JP | H232011510685 A | 4/2011 |
| JP | H232011517612 A | 6/2011 |
| JP | HEI25-2013504350 A | 7/2012 |
| WO | 1994026199 A1 | 11/1994 |
| WO | 2006031096 A1 | 3/2006 |
| WO | 2009146164 A1 | 12/2009 |
| WO | 2011001292 A1 | 1/2011 |
| WO | 2011029911 A1 | 3/2011 |
| WO | 2011117644 A1 | 9/2011 |
| WO | 2012021857 A1 | 2/2012 |
| WO | 2012058344 A1 | 3/2012 |
| WO | 2012058349 A1 | 3/2012 |
| WO | 2012068679 A1 | 5/2012 |
| WO | 2013043640 A1 | 3/2013 |
| WO | 2013152102 A1 | 10/2013 |
| WO | 2014177894 A1 | 11/2014 |

OTHER PUBLICATIONS

International Search Report dated Jun. 23, 2015 in connection with International Application PCT/GB2014/053304.
Japanese Office Action dated Jul. 20, 2018 in connection with Japanese App. No. 2016-554924.
Office Action dated May 2, 2018 in connection with Chinese Application No. 201480072820.X.

* cited by examiner

METHOD AND APPARATUS FOR USE IN THE PRODUCTION OF A SURGICAL GUIDE

CROSS-REFERENCE TO RELATED APPLICATIONS

This application is a continuation of International Application No. PCT/GB2014/053304 having a filing date of Nov. 5, 2014, entitled "Method and Apparatus for Use in the Production of a Surgical Guide", which is related to and claims priority benefits from U.K. patent application No. 1320745.1 filed on Nov. 25, 2013, also entitled "Method and Apparatus for Use in the Production of a Surgical Guide". The '304 international application and '745.1 U.K. application are hereby incorporated by reference herein in their entireties.

FIELD OF THE INVENTION

The present disclosure relates to a method and apparatus for use in the production of a surgical guide, for example in the intraoperative production of a surgical guide.

BACKGROUND OF THE INVENTION

Accurate placement is important to the success of many surgical implants and prostheses. Guidance devices for use in surgery have been developed to aid in placement. These systems often take the form of large and bulky robotic guides or navigation systems that can be registered to the patient's anatomy and the pre-operative imaging data. These systems are costly, significantly interrupt the surgeons work flow, require extensive set-up time, extra trained staff and are inconvenient to operate in the limited space of the modern operating theatre. These systems also require lengthy cleaning procedures and are often complicated to set up with the added risk that their digital nature makes them susceptible to errors while guiding the procedure.

Rapid manufacturing/prototyping techniques have been used effectively to produce simple bespoke guides that can be sterilized and brought into the surgical field. Such patient specific instrumentation is used in many surgical specialties such as dentistry, maxillofacial surgery and orthopedics. These guides have been shown to be useful in many different procedures as their bespoke nature allows them to be created to fit specifically onto a particular piece of anatomy in a similar manner to a jigsaw piece fitting a specific location. These guides, can, for example, be produced with holes or cutting slots to facilitate the guidance of surgical tools such as a drill during the procedure.

Previously, guides produced by rapid manufacturing/prototyping techniques have been time consuming to produce with long manufacturing times and logistics chains, often needing post production processing. Commercial 3D printing equipment is expensive and each printed guide had to be individually sterilized. The guides had to be produced in advance of the surgery and thus were unable to be modified once the operation had commenced if they were found to be problematic or the parameters of the operation were changed.

What is needed is an improved method and apparatus for use in the production of surgical guides.

SUMMARY OF INVENTION

A method of producing a modification plan for producing a surgical guide from an impression element can include:

obtaining surface data representing a configuration of a surface of an impression element providing an impression of a surgical site;

obtaining image data of a patient's anatomy;

obtaining surgical plan data providing a surgical plan with respect to features in the image data representing anatomical features of the patient's anatomy;

registering the impression element using the surface data and the image data with anatomical features of the patient's anatomy;

producing a modification plan from the surgical plan data using the registration of the impression element with anatomical features of the patient's anatomy, the modification plan being a plan for modifying the impression element.

In some embodiments, the modification plan is in accordance with the surgical plan data, that is to say that the modification plan is derived from the surgical plan data to enable a guide produced with the modification plan to guide surgery in accordance with the surgical plan.

In some embodiments, the surgical site can be an operatively exposed surgical site.

The modification plan is a plan of how to modify the impression element to produce a surgical guide. In some embodiments, the modification plan is a structural modification plan of how to structurally modify the impression element. In some embodiments, the modification plan is a tooling plan, a tooling plan being a plan of how to tool the impression element. In other embodiments, the modification plan is a plan of how to mark the impression element for example with guiding marks for subsequent cutting by hand. Tooling can include cutting or other methods of creating an opening, such as a gap or a hole, in the impression element, such as by cutting, drilling, milling, etc.

In some embodiments, the image data of the patient's anatomy includes image data of anatomical features in the vicinity of the surgical site. Generally, the image data is captured before the surgical site is exposed and therefore does not include image data directly relating to the exposure of the surgical site. The image data generally does not include the entirety of the patient's anatomy.

In some embodiments, the surgical plan is an electronic plan made, with reference to features of the image data which represent anatomical features of the patient's anatomy, defining how surgical interventions are to be made.

Registering two elements together includes calibrating how the features of one relate to the features of the other, for example by determining the configuration of both elements within a common coordinate system or frame of reference. For physical elements this is in general done by correlating data representing each element. Registration can be considered to provide a relative position.

In some embodiments, the impression element is registered directly with anatomical features, meaning it is not necessary for a reference marker to be inserted before the image data is captured.

In some embodiments, registering the impression element using the surface data and the image data with anatomical features of the patient's anatomy includes identifying, for a plurality of points on the surface of the impression element, a corresponding plurality of points on anatomical features of the patient, wherein a corresponding plurality of points on anatomical features of the patient are the plurality of points of the surgical site adjacent to the plurality of points on the impression element when the impression element is in place at the surgical site.

In some embodiments, registering the impression element using the surface data and the image data with anatomical features of the patient's anatomy includes registering the surface data with features in the image data which represent anatomical features of the patient's anatomy.

In some embodiments, registering the impression element using the surface data and the image data with anatomical features of the patient's anatomy includes identifying, for a plurality of points in the surface data representing points on the surface of the impression element, a plurality of points in the image data which represent corresponding points on anatomical features of the patient.

In some embodiments, a registration of an impression element with another object can include a determination of a relative position of a plurality of points on the surface of the impression element with respect to the other object.

In some embodiments, the impression element is a molded element, preferably molded by being placed against the surgical site.

In some embodiments, the modification plan includes instructions for operating a production apparatus to modify or to guide modification of the impression element.

In some embodiments, the instructions can be for presentation to a user to allow the user to operate the production apparatus.

In some embodiments, producing the modification plan includes producing a plan defined with respect to features of the surface data, representing features of the impression element. In other words, in such embodiments, the surgical plan defined with respect to features of the image data is converted to a plan defined with respect to features of the surface data using the registration of the surface data with features in the image data. This plan can be used to produce the instructions.

The instructions can be modification instructions, or they can be instructions to position a modification guide to guide an external modification tool.

In some embodiments, the method includes registering the impression element with the production apparatus using the surface data, the production apparatus including a modification tool for modifying the impression element or a modification guide for guiding a modification tool; wherein producing instructions includes producing instructions based on a calibrated position of the modification tool or modification guide and the registration of the impression element with the production apparatus.

In some embodiments, by registering the impression element with the production apparatus, the position of the impression element with respect to the production apparatus, for example in a receptor assembly, is calibrated. Therefore, desired modifications defined with respect to the impression element can be converted into modifications defined with respect to the production apparatus. By having the position of the modification tool or modification guide of the production apparatus calibrated, these modifications defined with respect to the production apparatus can be converted into instructions for the production apparatus, for example operation instructions defining how to operate the modification tool to make the desired modifications to the impression element, or instructions defining how to position the modification guide to enable such desired modifications to be made.

In some embodiments, registering the impression element with the production apparatus includes registering the surface data with data representing a structure of the production apparatus. Producing instructions can include converting a plan defined with respect to features of the surface data into a plan defined with respect to data representing a structure of the production apparatus by using the registration of the surface data with data representing a structure of the production apparatus. Using the calibration of the position of the modification tool or modification guide, this can be converted into instructions for use of the modification tool or modification guide, such as operation instructions governing the operation of the modification tool or modification guide.

In some embodiments, registering the impression element with the production apparatus uses data representing a relative position of a surface configuration recorder with respect to the production apparatus. In other embodiments, this registration can use a predetermined relative position with respect to the production apparatus of a feature in the surface data, for example surface data representing a reference element of a carrier.

The instructions can include instructions concerning how to move the impression element and/or modification guide and/or how to operate the modification tool.

The instructions provide how to modify the impression element, or how to guide modification of the impression element, to produce a guide to guide surgery according to the surgical plan.

In some embodiments, the method includes registering the impression element with a carrier carrying the impression element using the surface data.

In some embodiments, registering the impression element with a carrier includes using a calibration of a position of the carrier during the recording of the surface data for example with respect to the production apparatus. In some embodiments, the production apparatus can include a receptor assembly configured to hold the carrier in a predetermined relative position during the recording of the surface data and during modification of the impression element. In other embodiments, the surface data can include data representing a reference element of the carrier.

The carrier can have a predetermined configuration.

In some embodiments, registering the impression element with a carrier includes registering the surface data with data representing a structure or configuration of the carrier.

In some embodiments, obtaining surface data includes operating a scanner to scan the surface of the impression element. In other embodiments, the surface data can be obtained by touching a digitizer arm against a plurality of points on the surface of the impression element.

Where the surface data is obtained from a scanner, the surface data can include data representing distance from the scanner to a plurality of points on the on the surface of the impression element.

Preferably, the scanner is an optical scanner since this is a precise way of scanning, and offers greater precision than CT scans.

A method of producing a surgical guide can include:
producing a modification plan as above, wherein obtaining surface data includes operating a surface configuration recorder to obtain the surface data; and
modifying the impression element in accordance with the modification plan.

Preferably, the surface configuration recorder is a scanner.

Preferably, modifying the impression element in accordance with the modification plan includes operating a production apparatus to modify the impression element, or to guide modification of the impression element, in accordance with the modification plan to produce the surgical guide.

In some embodiments, operating the production apparatus is in accordance with the instructions discussed above.

Preferably, operating the production apparatus includes operating a modification tool of the production apparatus, operating a modification tool preferably including one or more of cutting, drilling and milling.

In other embodiments, operating the production apparatus can include operating a modification guide.

The method preferably includes placing a moldable element against the surgical site to form the impression element.

A moldable element for use in surgery can include:

moldable material for being placed against a surgical site to form an impression of that site; and a reference element coupled to the moldable material for allowing a configuration of a surface of the moldable material to be recorded with respect to a known point of reference.

The moldable element preferably includes a carrier for carrying the moldable material, the carrier including the reference element.

The reference element preferably includes a coupling element for coupling the carrier to a production apparatus in a predetermined position.

The carrier can include an identification element, the identification element optionally identifying a particular patient or a particular surgical procedure with which the moldable element is to be used.

In some embodiments, the carrier includes a body and at least one registration arm extending from the body, the at least one registration arm being fixed with respect to the body, the at least one registration arm being operable to register contact with bone whereby to assist registration of the moldable element with anatomical features of a patient by providing information relating to a position of bone with respect to the body of the carrier when the carrier is in place at a surgical site.

In some embodiments, the carrier includes a coupling element for coupling to a guiding element for guiding a surgical component to interact with a surgical site.

In some embodiments, the carrier includes a guiding element for guiding a surgical component to interact with a surgical site.

In some embodiments, the carrier includes a body and the guiding element is provided on an arm extending from the body.

In some embodiments, the guiding element is fixed with respect to the body.

The guiding element is preferably selectively configurable.

In some embodiments, the guiding element can be selectively configured into a plurality of different configurations, for example the guiding element can be or can include a component which can be aligned in a plurality of orientations, and/or positioned in a plurality of positions.

Preferably, the guiding element includes a surgical tool for being guided by the respective guiding element.

In some embodiments, the guiding element includes a screw guide for guiding a screw to be screwed into a surgical site, the screw guide enabling registration of a screw screwed into a surgical site with anatomical features of a patient.

In some embodiments, the moldable material includes a first surface designed to receive an impression of a surgical site and to be scanned, and wherein the reference element includes a projection projecting laterally beyond a side of the first surface whereby to be included in a scan of the first surface.

In some embodiments, the reference element can include one or more arms extending from the carrier. Having both the first surface and the reference element recorded means that the configuration of the first surface can be determined with respect to the reference element.

In some embodiments, the moldable material includes an outer layer of thermoplastic material and an inner layer of permanently deformable material.

The thermoplastic material preferably has a transition temperature below a tissue damaging threshold.

A surgical guide or jig can include a moldable element as above having been molded to form an impression of a surgical site to provide a tissue fitting surface, and modified, preferably cut, drilled, or prepared, to provide a guide for a surgical tool.

An impression element holder can include:

a first coupling element for coupling the holder into a production apparatus in a predetermined position;

a second coupling element for coupling an impression element into the holder in a predetermined position;

a receiving zone for receiving an impression element coupled to the second coupling element without contact with a production apparatus coupled to the first coupling element.

The impression element holder preferably includes an open side to allow an impression element held within the holder to be optically scanned.

A production apparatus for the production of a surgical guide can include:

a receptor assembly having received therein an impression element conforming to a shape of a surgical site; and a modification tool for modifying the impression element or a modification guide for guiding a modification tool; wherein the modification tool or modification guide and the impression element are positionable in a plurality of predetermined relative positions to allow the impression element to be modified in accordance with a modification plan, wherein a modification plan is a plan for modifying the impression element and is derived from a surgical plan and a registration of the impression element with anatomical features of a patient's anatomy.

A production apparatus for the production of a surgical guide can include:

a receptor assembly for receiving an impression element conforming to a shape of a surgical site;

a surface configuration recorder for recording a configuration of a surface of an impression element received by the receptor assembly to produce surface data for registering that impression element with anatomical features of a patient's anatomy and with the production apparatus; and a modification tool for modifying an impression element received by the receptor assembly or a modification guide for guiding a modification tool; wherein the modification tool or modification guide and an impression element received by the receptor assembly are positionable in a plurality of predetermined relative positions to allow an impression element received by the receptor assembly to be modified in accordance with a modification plan, wherein a modification plan is a plan for modifying an impression element and is derived from a surgical plan and a registration of that impression element with anatomical features of a respective patient's anatomy.

Preferably, the surface configuration recorder is a scanner, preferably an optical scanner.

Preferably, the modification tool includes one or more of a cutter for cutting an impression element, a drill for drilling an impression element, a milling component for milling an impression element, a slot saw for sawing, and a marker for marking an impression element.

The apparatus preferably includes:

a processor for determining, from a modification plan and a registration of the apparatus with an impression element received by the receptor assembly, a desired relative position of the modification tool or modification guide with respect to that impression element to enable that impression element to be modified in accordance with that modification plan.

In some embodiments, the processor is operable to obtain a modification plan from an external computing device.

In some embodiments, the processor is operable to obtain patient registration data providing a registration of an impression element received by the receptor assembly with anatomical features of a respective patient's anatomy, wherein the processor is operable to obtain a surgical plan, and wherein the processor is operable to calculate a modification plan from the patient registration data and the surgical plan.

In some embodiments, a registration of an impression element with anatomical features of a patient's anatomy includes a registration of surface data representing a configuration of a surface of that impression element with features of image data representing anatomical features of a patient's anatomy. This can include an identification, for a plurality of points in the surface data representing points on the surface of the impression element, with a plurality of points in the image data which represent corresponding points on anatomical features of the patient.

Preferably, the processor is operable to determine how to modify an impression element in accordance with the surgical plan by using the patient registration data to determine how a respective impression element will align with a surgical site, and thereby determining how to modify an impression element in order to provide a configuration at a surgical site that is in accordance with the surgical plan.

Preferably, the processor is operable to determine patient registration data from image data of a patient's anatomy and surface data from the surface configuration recorder.

In some embodiments, the processor is operable to register an impression element received in the receptor assembly with the production apparatus, preferably with the receptor assembly, using surface data from the surface configuration recorder.

The processor can be calibrated with a relative position of the surface configuration recorder, and the modification tool or modification guide.

The processor can be operable to adapt its calibration in response to movement of the surface configuration recorder and/or modification tool and/or modification guide.

The apparatus can include a control unit operable to adjust a relative position of the modification tool or modification guide with respect to an impression element received by the receptor assembly in order to place them in a desired relative position.

The relative position of the modification tool or modification guide with respect to an impression element received by the receptor assembly can be adjusted by adjusting the relative position of the modification tool or modification guide with respect to the receptor assembly, which can include adjusting the position of the modification tool or modification guide and/or the receptor assembly.

The control unit can include the processor. The processor and/or control unit can be configured to perform the method above.

In some embodiments, the control unit is operable to adjust a position of the receptor assembly and/or the modification tool or modification guide to enable modification in accordance with a modification plan.

In some embodiments, the control unit is operable to control the modification tool to modify an impression element received by the receptor assembly in accordance with a respective modification plan.

In some embodiments, the control unit is calibrated with relative positions of the surface configuration recorder and of the modification tool or modification guide and optionally of the receptor assembly.

In some embodiments, the control unit is operable to adapt its calibration in response to movement of the surface configuration recorder and/or receptor assembly and/or modification tool and/or modification guide.

Preferably, the control unit is operable to obtain spatial registration data providing a registration of an impression element received by the receptor assembly with the apparatus, and wherein the control unit is operable to control the modification tool to modify a received impression element in accordance with a modification plan using the spatial registration data.

Preferably, the receptor assembly includes a coupling or attachment element to cooperate with a corresponding coupling or attachment element on an impression element.

Preferably, the receptor assembly is configured to receive an impression element holder for holding an impression element without contact with the apparatus to prevent, or at least reduce, contamination of a received impression element or the apparatus.

In some embodiments, the modification tool can releasably hold a tool element to enable a used tool element to be substituted for a new sterile tool element.

The tool element can for example be a cutting element for a cutter, a drill bit for a drill, a milling component head for a milling component, a marker element for a marker, or a saw element for a saw.

The apparatus can include a motor for moving the modification tool or modification guide.

The apparatus can include a motor for moving the receptor assembly.

A method can include:

obtaining from a surface configuration recorder surface data representing a configuration of a surface of an impression element providing an impression of a surgical site;

obtaining data relating to a relative position of a location for the guiding element with respect to the surface;

obtaining image data of a patient's anatomy;

registering the impression element with the location for the guiding element using the surface data and the data relating to the relative position of the location for the guiding element with respect to the surface;

registering the impression element using the surface data and the image data with anatomical features of the patient's anatomy;

registering the guiding element with anatomical features of the patient's anatomy using the registration of the impression element with anatomical features of the patient's anatomy and the registration of the impression element with the location for the guiding element.

The guiding element can be at the location for the guiding element during recordal, or the guiding element can have been removed before recordal of the surface data.

The data relating to a relative position of the location for the guiding element with respect to the surface can include data relating to a relative position of the location for the guiding element with respect to the surface configuration recorder.

The data relating to a relative position of the location for the guiding element with respect to the surface can include data identifying features in the surface data representing the location of the guiding element or it can include data identifying features in the surface data representing a reference marker and data providing a relative position of the location for the guiding element with respect to the reference marker. In other words, obtaining data relating to a relative position of the location for the guiding element with respect to the surface can include determining from the surface data a relative position of a reference marker and/or the location of the guiding element with respect to the surface.

In some embodiments, the data relating to a relative position of the location for the guiding element with respect to the surface includes data relating to a relative position, during the recordal of the surface data, of the surface and a carrier carrying the impression element, wherein the carrier includes or can receive the guiding element; and wherein registering the impression element with the guiding element includes registering the impression element with the carrier using the surface data and the data relating to the relative position of the surface and the carrier.

In some embodiments, obtaining data relating to a relative position of the surface and the carrier includes determining from the surface data a relative position of a reference element of the carrier with respect to the surface.

In some embodiments, the guiding element is configurable, and the method includes:

obtaining surgical plan data providing a surgical plan with respect to features in the image data representing anatomical features of the patient's anatomy;

determining a configuration for the guiding element from the surgical plan data using the registration of the location for the guiding element with anatomical features of the patient's anatomy.

In some embodiments, registering the guiding element with anatomical features of the patient's anatomy includes registering data relating to each of the plurality of configurations of the guiding element with features in the image data representing anatomical features.

The method can include configuring the guiding element in accordance with the determined configuration.

The method can include guiding the surgical component using the guiding element to perform a surgical interaction with the patient.

A method of registering a guiding element with a patient's anatomy can include:

obtaining from a surface configuration recorder surface data representing a configuration of a surface of an impression element providing an impression of a surgical site;

obtaining data relating to a relative position during the recordal of the surface data of the surface configuration recorder and a carrier carrying the impression element, wherein the carrier includes or can receive a guiding element for guiding a surgical component;

obtaining image data of a patient's anatomy;

registering the impression element with the carrier using the surface data and the data relating to the relative position of the surface configuration recorder and the carrier;

registering the impression element using the surface data and the image data with anatomical features of the patient's anatomy;

registering the guiding element with anatomical features of the patient's anatomy using the registration of the impression element with anatomical features of the patient's anatomy and the registration of the impression element with the carrier.

In some embodiments, registering the impression element with the carrier includes registering the surface data with data relating to a structure or configuration of the carrier.

In some embodiments, registering the guiding element with anatomical features of the patient's anatomy uses data relating to a position of the guiding element, for example with respect to the carrier.

In some embodiments, registering the guiding element with anatomical features of the patient's anatomy includes registering data relating to a structure of the guiding element with features of the image data representing anatomical features.

Preferably, the guiding element is configurable, and the method includes:

obtaining surgical plan data providing a surgical plan with respect to features in the image data representing anatomical features of the patient's anatomy;

determining a configuration for the guiding element from the surgical plan data using the registration of the impression element with anatomical features of the patient's anatomy.

In some embodiments, registering the guiding element with anatomical features of the patient's anatomy uses data relating to a position with respect to the carrier when the guiding element is coupled to the carrier of those parts of the guiding element that are fixed with respect to the carrier when the guiding element is coupled to the carrier.

In other embodiments, registering the guiding element with anatomical features of the patient's anatomy uses data relating to each of the plurality of configurations of the guiding element with respect to the carrier when the guiding element is coupled to the carrier.

The method can include configuring the guiding element in accordance with the determined configuration.

In some embodiments, the configuration for the guiding element is determined in accordance with the surgical plan data, that is to say that the configuration is derived from the surgical plan data to enable the guiding element to guide surgery in accordance with the surgical plan.

In some embodiments, the surgical component can be a surgical tool and the guiding element can include the surgical tool that the guiding element is configured to guide to enable surgery to be carried out in accordance with the surgical plan.

In some embodiments, obtaining data relating to a relative position during the recordal of the surface data of the surface configuration recorder and the carrier includes determining from the surface data a relative position of a reference element of the carrier with respect to the surface or surface configuration recorder.

In some embodiments, the reference element has a known position with respect to the carrier as a whole, and the position of the carrier with respect to the surface or surface configuration recorder can thereby be determined.

The method can include guiding the surgical component using the guiding element to perform a surgical interaction with the patient.

In some embodiments, a surgical screw or other marker can be attached to the patient's anatomy using the guiding element, and that marker can be registered to anatomical features of the patient's anatomy, thereby enabling that marker to be used as a reference point for surgical navigation or guidance.

A registration apparatus for use in the registration of a guiding element with a patient's anatomy can include:

a receptor assembly including a coupling element for coupling to a coupling element on a carrier for an impression element whereby to hold a carrier for an impression element in a predetermined position; and a surface configuration recorder for recording a configuration on a surface of an impression element carried by a carrier received by the receptor assembly to produce surface data for registering that impression element with anatomical features of a patient's anatomy and with that carrier and thereby for registering that carrier with anatomical features of a patient's anatomy.

A kit for producing a surgical guide can include:

an apparatus as above; and at least one impression element being a moldable element as above.

In other embodiments, a kit for producing a surgical guide can included:

an apparatus as above; and moldable material for placing against a surgical site to form an impression element.

The kit preferably includes at least one carrier for being attached to the or a part of the moldable material to carry the moldable material.

In some embodiment a computer program can perform the method(s) described above when executed on a computing device.

A programmable guiding element for guiding a surgical intervention can include:

a coupling element for coupling the guiding element to a carrier for an impression element; and a tool guide selectively configurable in a plurality of configurations for guiding a tool to make a surgical intervention, wherein each of the plurality of configurations provides the tool guide in a different predetermined position with respect to the coupling element.

The guiding element can include a surgical tool to be guided by the tool guide.

A method can include:

obtaining surface data representing a configuration of a surface of an impression element providing an impression of a surgical site;

obtaining image data of a patient's anatomy; and registering the impression element using the surface data and the image data with anatomical features of the patient's anatomy.

In some embodiments, the carrier can be used to temporarily attach the impression element to other surgical tools such that the impression element can be molded to surgical anatomy in difficult to reach places for example.

In some embodiments, a moldable material can be placed in a surgical site in order to form an impression of that site. The material can then be placed in an apparatus which can scan the impressed surface of the moldable material. The apparatus is calibrated so that it can spatially register the scan with the apparatus. For example, the moldable material can be attached to a carrier component and the material can be placed in the apparatus by connecting an attachment element on the carrier component to a corresponding element in the apparatus so that the material is in a pre-calibrated location within the apparatus. The scanner can also be in a predetermined calibrated position within the apparatus enabling a determination from the scan of the position of the material with respect to carrier component and hence with respect to the rest of the apparatus. Using the fact that the material is known to fit against a surgical site, the scanned material can be spatially registered with image data of the patient. A surgical plan which dictates how surgery at the surgical site should proceed can then be converted into a plan as to how to modify, for example cut, the material to form a guide to guide the surgery. The apparatus can either serve as a marker to mark or guide modification, for example cutting, of the material, or it can itself modify the material in accordance with the modification plan. The modified material, when placed back into the surgical site, can thus act as a surgical guide.

It is to be appreciated that certain embodiments can be incorporated as code (e.g., a software algorithm or program) residing in firmware and/or on computer useable medium having control logic for enabling execution on a computer system having a computer processor. Such a computer system typically includes memory storage configured to provide output from execution of the code which configures a processor in accordance with the execution. The code can be arranged as firmware or software, and can be organized as a set of modules such as discrete code modules, function calls, procedure calls or objects in an object-oriented programming environment. If implemented using modules, the code can comprise a single module or a plurality of modules that operate in cooperation with one another.

In some embodiments, guides produced via the methods and apparatuses disclosed her can be produced intraoperatively directly from an impression of the surgical site, thereby minimizing manufacturing time and logistics chains, removing the expense of 3D printing equipment, and enabling custom guides to be manufactured or modified during surgery in accordance with the desired procedure.

Preferred embodiments use a surgical navigation registration technique and associated apparatus for the intraoperative manufacture of a bespoke guide to facilitate the placement, operation or use, of a surgical tool, implant or accessory.

Some embodiments can provide a cost effective system capable of producing patient specific surgical guides with minimal production time. Bespoke guides can be produced intraoperatively without extended set up time, cleaning or interruption to the surgical workflow.

DETAILED DESCRIPTION OF PREFERRED EMBODIMENT(S)

Figure 1:
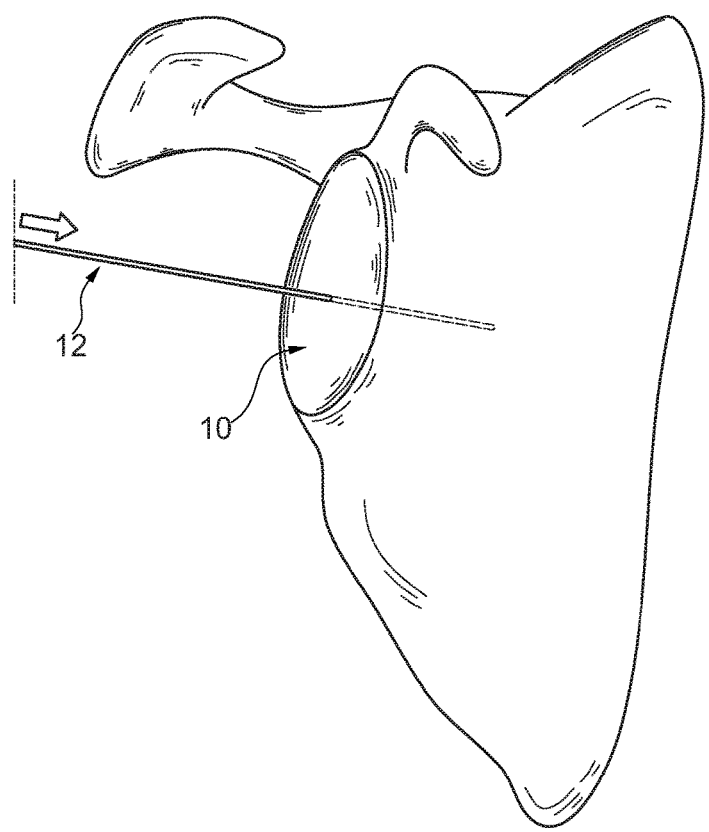
FIG. 1 is a diagram showing a planned placement for a guide wire in a scapula.
Figure 2A:
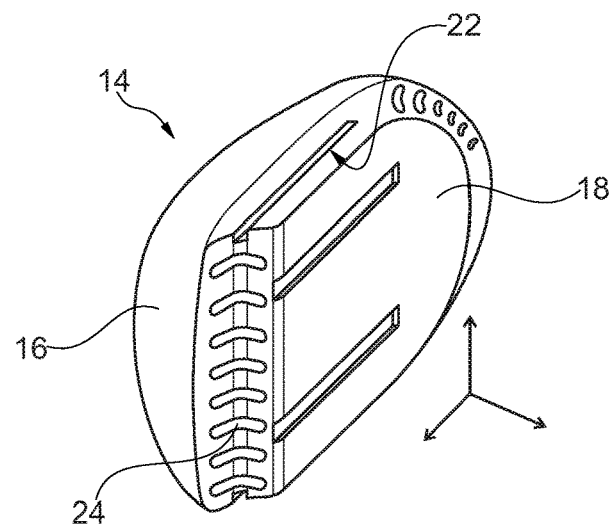
FIGS. 2A and 2B are, respectively, a perspective and side view of a guide blank.
Figure 2B:
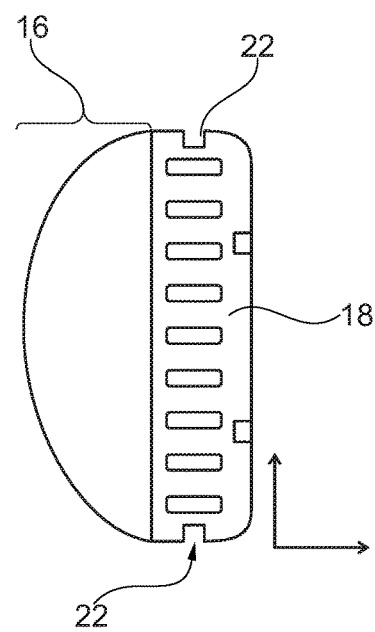

The above drawings are schematic only and not to scale. Embodiments are described within the framework of the total shoulder arthroplasty procedure, with specific focus on a method for orientating the glenoid component of the prosthesis within the glenoid cavity of scapula 10 as shown in FIG. 1. However, some embodiments can also be used for other surgical procedures, for example for different parts of the human body including dental surgery, or for the body of a different animal, and/or with different guiding structures.

As commonly practiced in many surgical fields; once preoperative imaging data such as an MRI or CT scan has been obtained, a surgeon can pre-operatively digitally plan the procedure to be performed using software planning tools. Such software can produce a prescription for the procedure. For the purposes of this description, it is assumed that such a prescription in the form of a suitable digital plan (DP) defines the placement of guide wire 12 into the glenoid cavity of scapula 10.

In other embodiments, a digital plan can define various other surgical interventions to be made. The digital plan defines a surgical procedure with respect to features in the pre-operative imaging data representing anatomical features of the patient.

In total shoulder arthroplasty, the guide wire is a commonly used piece of hardware that is drilled into bone to define the axis and location of a hole that can be drilled into the glenoid in order to affix the glenoid component of the joint prosthesis into place. Once in position, the guide wire is drilled over with a cannulated drill bit and removed to create the hole for the implant stalk. In this way the axis and position of the implant stalk is consequentially defined.

In the embodiments shown in FIGS. 2 to 7, guide blank 14 is provided including modifiable or moldable element 16, and rigid carrier 18 for carrying moldable element 16.

Guide blank 14 can also be referred to as a registration tool since it can be registered to a production apparatus and anatomical features of a patient.

Guide blank 14 is later on in the workflow inserted into and adapted by production apparatus 20 (shown for example in FIG. 3) which is able to modify guide blank 14 to rapidly form a bespoke guide to facilitate the placement of guide wire 12.

Moldable element 16 can be a temporarily moldable element made up, for example, of a material that, once activated, is initially pliable and can eventually harden over time or in the presence of a catalyst or other setting initiator such as a bright light of particular wavelength or exposure to atmospheric air. In other embodiments, moldable element 16 can be a non-hardening moldable material, although in some embodiments this is not preferred since there can be a risk of moldable element 16 being undesirably deformed during further processing.

The moldable material is contained, retained, and incorporated within the carrier.

Moldable element 16 can be molded by being pressed into a surgical site, after which it can be considered to be an impression element, as it can provide an impression of the surgical site.

Carrier 18 includes a coupling arrangement by which guide blank 14 can be coupled into production apparatus 20 in a predetermined position.

In the embodiments shown in FIGS. 2-7, the coupling arrangement includes guides in the form of channels 22 which can receive counterpart guides in the form of ridges in order to couple guide blank 14 to production apparatus 20. In other embodiments, the coupling arrangement can include a clip or other attachment mechanism.

In the embodiments shown in FIGS. 2-7, carrier 18 is a standardized component that has features that are compatible with features of production apparatus 20. By providing carrier 18 as a standardized component, it is easier to ensure, or at least increase the likelihood, that carrier 18 easily fits into a receptor assembly of a production apparatus in a known predetermined position.

Carrier 18 can incorporate additional features such as finger rests, grips 24, or fixings for additional associated instrumentation.

In some embodiments, a variety of sterile pre-packaged guide blanks can be offered, compatible with and reflecting the various sizes of surgical sites that surgeons face. For the embodiment shown in FIGS. 2-7, a guide blank of the appropriate size and shape for the purpose of a shoulder replacement will be selected. In this case, one that is roughly the shape of the average human glenoid cavity.

Figure 3:
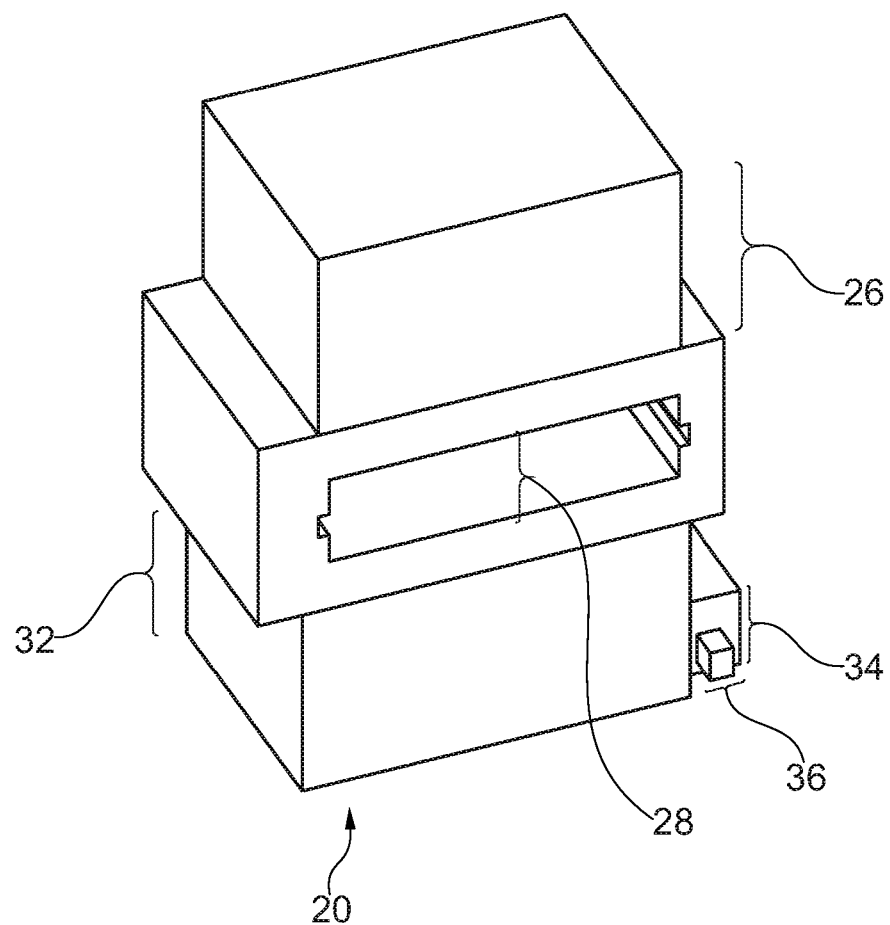
FIG. 3 is a perspective view of a production apparatus.
Figure 4:
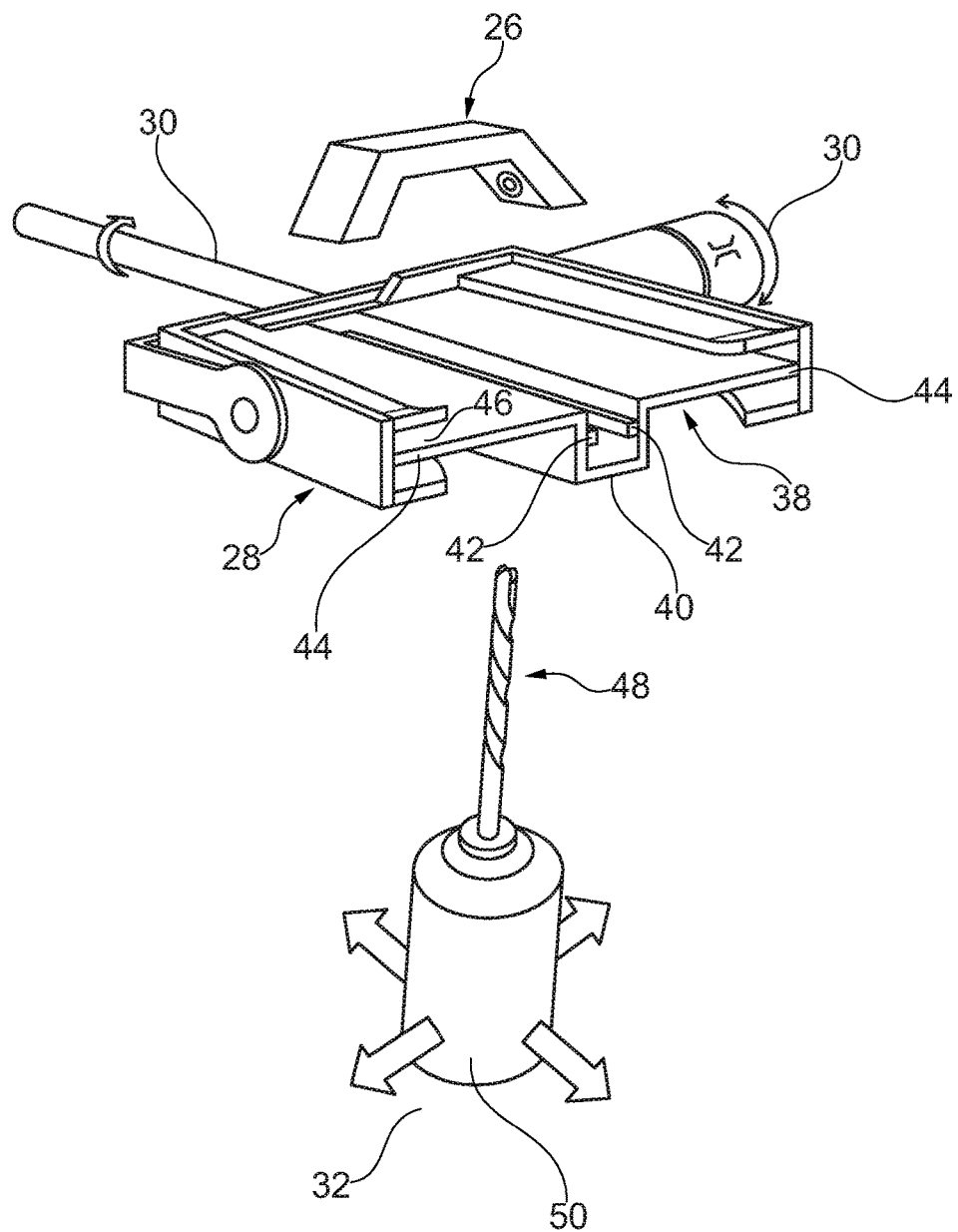
FIG. 4 is a perspective view of a receptor assembly and modification tool for the production of the production apparatus shown in FIG. 3.

In the embodiment shown in FIGS. 2-7, production apparatus 20 includes the following elements as shown in FIGS. 3 and 4:

scanner 26 to create a detailed 3D surface scan of an object. This can for example be an optical 3D scanner;

receptor assembly 28 capable of receiving guide blank 14;

adjustment mechanism 30 operable to manipulate and the position of receptor assembly 28 (and thereby also a guide blank received in the receptor assembly) with respect to modification tool 32;

modification tool 32 capable of independent movement with respect to receptor assembly 28 (and thereby also with respect to a guide blank received in the receptor assembly) and operable to modify guide blank 14 when received in receptor assembly 28;

control unit 34, such as a microprocessor control unit, designed, suitably connected and powered such that it can control the functioning of production apparatus 20; and/or communication element 36, for example with wireless connection capabilities, such that the production apparatus can be given external commands by an operator and obtain data.

It is not necessary to have adjustment mechanism 30. In some embodiments modification tool 32 can provide the necessary relative movement.

Scanner 26 is arranged to face receptor assembly 28 thereby to be able to scan impression element 16 of guide blank 14 received therein.

Adjustment mechanism 30 is configured to manipulate and orientate the position of receptor assembly 28 (and thereby also a guide blank received in the receptor assembly) with respect to scanner 26 to enable scanner 26 to scan most of, if not the entire, surface of impression element 16 and in some embodiments to scan at least a part of carrier 18.

Control unit 34 is calibrated with the relative position of the scanner with respect to at least one reference point. In some embodiments, the receptor assembly provides a reference point although reference points can be provided by other parts of the production apparatus. In some embodiments, the receptor assembly does not provide a reference point but is itself calibrated with respect to the one or more reference points.

Control unit 34 can therefore determine from a scan by the scanner the position of the impression element of a guide blank in the receptor assembly with respect to the one or more reference points of the production apparatus, thereby registering the impression element to the production apparatus. In the embodiment shown in FIGS. 2-7, because carrier 18 is a standardized component, that is to say it has a predetermined configuration, and is received only in a predetermined position in the receptor assembly, the guide blank, including the carrier, is effectively registered to the production apparatus.

As described above, control unit 34 is operable to control the position of receptor assembly 28 using adjustment mechanism 30, for example to enable the whole of the impression element to be scanned. The control unit is configured to compensate for such movements of the receptor assembly when registering the impression element with the production apparatus.

The control unit is also calibrated with the relative position of the modification tool with respect to the one or more reference points and thereby with respect to the production apparatus. Once the impression element has been registered to the production apparatus, the control unit can therefore also determine the position of the modification tool with respect to the impression element, enabling the control unit to manipulate the modification tool and the adjustment mechanism to make a desired modification to a guide blank.

In some embodiments, as components within the production apparatus move relative to each other, for example as a result of movement of the modification tool or operation of the adjustment mechanism, control unit 34 is configured to adjust its calibration.

As described above, the modification tool is movable with respect to the receptor assembly. The modification tool can be moved to come into contact with a guide blank in the receptor assembly whereby to modify the guide blank in a controlled manner.

The modification tool can for example include a CNC drill, cutting device or other modifier, depending on the type of modification to be made to the guide blank. In some embodiments, the modification tool does not structurally modify the guide blank, but simply marks it. In such embodiments, the modification tool can include a marker to mark the guide blank to show where structural modifications should be made, and these structural modifications can be made subsequently by hand.

Production apparatus 20 is a sealed self-contained, reusable unit. For this reason, parts of the production apparatus that comes into contact with material that will touch human tissue should be easily disposed of and replaced in order to maintain sterility.

As described above, the production apparatus includes receptor assembly 20 into which guide blank 14 is able to be attached once it has received an impression of a surgical site. In some embodiments, receptor assembly 20 is located centrally within the production apparatus, although other positions are possible.

Once the patient's anatomy has been suitably dissected in the usual fashion to expose the surgical site, in this case the glenoid cavity as shown in FIG. 1, guide blank 14 is used to begin the guidance process.

The deformable area of guide blank 14—moldable element 16—is suitably activated while guide blank 14 is firmly pressed into the glenoid cavity allowing the deformable surface to mold to the shape and form an impression of the glenoid cavity and any exposed edges. This process can be seen in FIG. 6. Position 100 shows guide blank 14 being pressed into the surgical site to form an impression. In some embodiments, it is preferable to have as much contact as possible between the moldable area of the guide blank and the bony anatomy that can be safely exposed.

Once moldable element 16 has set and become a firm impression element, guide blank 14 with integral moldable element, having been molded to the shape of the glenoid, can be removed from the surgical field and the next stage of the process can begin.

In order to aid later relocation of the guide blank, provision can be made for screwing or pinning of the guide blank into place, perhaps at the time that the moldable material is setting.

Guide blank holder 38, which in some embodiments can be referred to as an enclosure lining, is then inserted into receptor assembly 28 of the production apparatus. In some embodiments, guide blank holder 38 is single use and sterile and includes guide blank coupling element 40 to couple a guide blank into the guide blank holder 38 in a predetermined relative position so that the guide blank is received in receiving zone 41 without contact with the production apparatus. In the embodiments shown in FIGS. 2-7, the guide blank coupling element includes channel 43 including first and second ridges 42 for coupling to first and second channels on carrier 18 of guide blank 14, although other coupling or attachment mechanisms can be used in other embodiments.

The guide blank holder also includes at least one receptor assembly coupling arrangement for coupling the guide blank holder into a holder coupling arrangement of the receptor assembly so that the guide blank holder is held in a predetermined relative position without the guide blank contacting the production apparatus. In the embodiments shown in FIGS. 2-7, the at least one receptor assembly coupling arrangement includes first and second flanges 44 for being received in a holder coupling arrangement including first and second channels 46 of the receptor assembly.

In the embodiment shown in FIGS. 2-7, guide blank holder 38 is a standardized component and control unit 34 is calibrated with dimensions of guide blank holder 38 and carrier 18 whereby control unit 34 is calibrated with the relative position of carrier 18 and holder 38 with respect to the one or more reference points, and thereby to the production apparatus, when inserted into the receptor assembly.

Guide blank 14 is inserted into receptor assembly 28 of production apparatus 20, in particular into guide blank holder 38, itself separate from, in the sense of non-integral with and removable from, the production apparatus assembly.

Guide blank 14 is fastened into place in a fixed predetermined position with respect to the receptor assembly as defined by the standardized construction of both the receptor assembly and the guide blank holder. In other words, when inserted into the guide blank holder, the carrier of the guide blank is in a predetermined position with respect to the receptor assembly.

Figure 5:
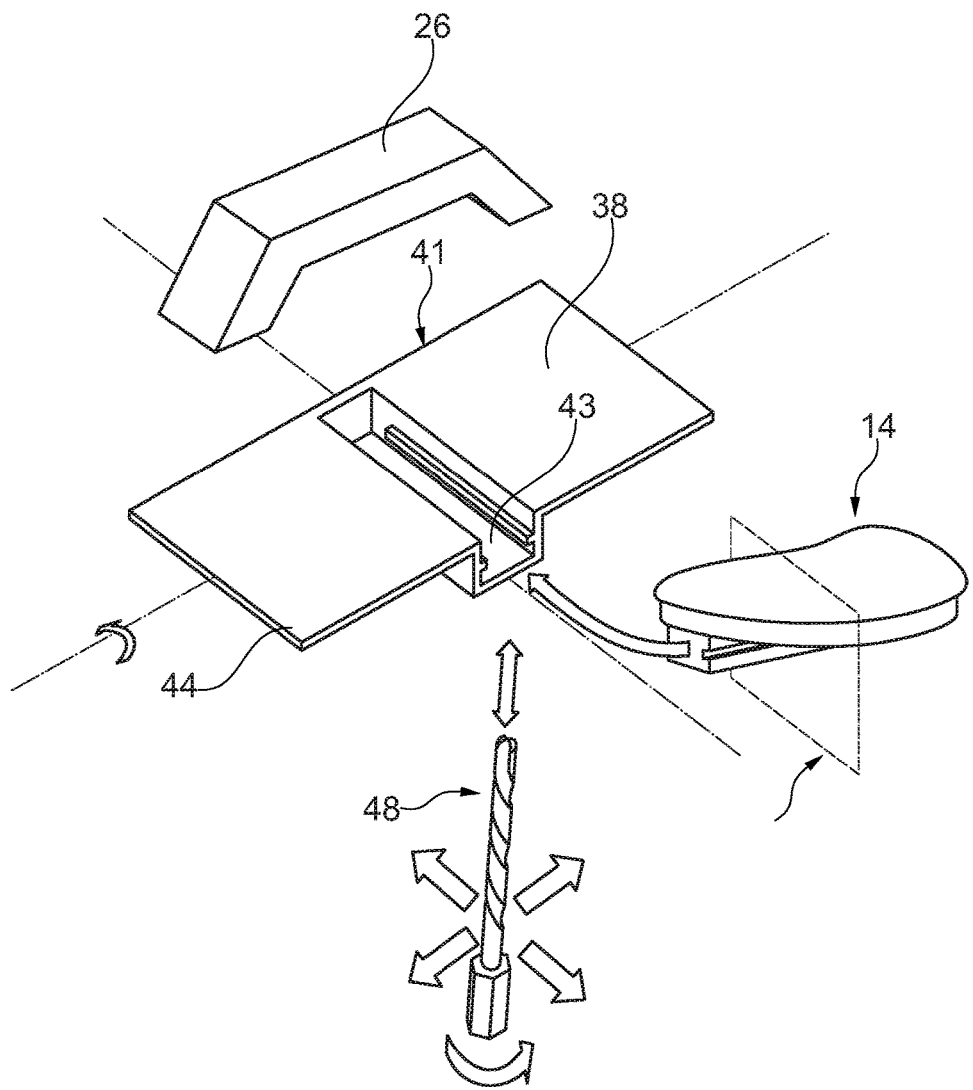
FIG. 5 is an exploded view showing the insertion of the guide blank of FIG. 2 into the production apparatus of FIG. 3.

While the surfaces of the receptor assembly are not sterile, the guide blank holder is placed into the aperture by a sterile agent such that when it is affixed within the production apparatus, the surfaces of the guide blank holder not in contact with the production apparatus remain sterile. Guide blank 14 can now be inserted into its corresponding coupling element 40 in the guide blank holder and also remain sterile as shown in FIG. 5.

Once the prepared guide blank has been affixed in the above way, the assembly including the production apparatus, guide blank holder and guide blank is now initiated.

Microprocessor control unit 34 of the production apparatus now can wirelessly or otherwise connect via communication element 36 with one or more computers including the digital plan and the medical imaging data relating to the particular patient such as CT scan data. For example, this can be the computer used by the surgeon to plan the procedure they wish to undertake. The digital plan or prescription for the operation can be downloaded into control unit 34 of the production apparatus.

Guide blank 14 is anchored in place within guide blank holder 38 in receptor assembly 28 such that impression element 16 faces towards 3D surface scanner 26 within the production apparatus.

The 3D surface scanner is mounted in a fixed position thus the microprocessor is programmed with an inherent knowledge of the spatial relation between the surface scanner and the position of the receptor assembly containing the guide blank holder and the guide blank.

The surface scanner scans in the direction of impression element 16 of guide blank 14, thus forming a 3D surface model of impression element 16. If required, the receptor assembly can manipulate guide blank 14 in several axes, with the use of integrated servo motors or otherwise, for example using adjustment mechanism 30, to maximally expose most, if not all, surfaces of the impression element to the scanner.

Because control unit 34 is calibrated with the relative positions of the scanner and the one or more reference points, control unit 34 can determine the relative position of the impression element with respect to the one or more reference points and can thereby co-register the 3D surface topography of the impression element with the production apparatus. Because in this embodiment carrier 18 and guide blank holder are standardized components, control unit 34 can register the impression element with the carrier and with the guide blank holder. The control unit can also register the impression element with the receptor assembly within the production apparatus.

This co-registration is facilitated by the interposition of 3D data from the scanner alongside the pre-determined geometry of the carrier, guide blank holder and production apparatus assembly with respect to the 3D scanner. This process can be further explained if the impression element were to be removed from the guide blank such that only carrier 18 were to remain affixed within the guide blank holder within the production apparatus; the scanner would produce 3D data identical to its pre-programmed 'knowledge' of the geometry within the production apparatus regardless of the spatial configuration of the assembly. If the impression element is now added, the scan will produce data with a 'body'—the impression element, obscuring the aforementioned 'standard geometry picture' that would have been seen from the point of view of the 3D scanner. The distance from the scanner surface to points of the impression element surface will inherently be calculable thus this data can be used to produce a virtual model 'within' the production apparatus processor, of the position and shape of the impression element surface with respect to the carrier of the guide blank, the guide blank holder and the production apparatus aperture assembly; thus spatially registering the geometry.

To be surgically useful, the components should be co-registered with anatomical features of patient anatomy as defined by pre-operative image data. A computer program is executed either on an associated computer or the inbuilt processor within the production apparatus. This program analyses the 3D scan data of the impression element and compares it to the imported CT scan data in the following way. It is given that the majority of the impression element will be the impression caused by pressing the impression element to the native bony anatomy within the surgical field; in the case of this embodiment, that of the glenoid cavity (FIG. 1) surface. An individual's bony anatomy is unique is shape, in addition to this, wear and tear has often removed the majority of the cartilage from the surface of the joint and osteoarthritis has deformed the surface into a topographically unique geometry. In the case of the total shoulder arthroplasty (TSA), the glenoid labrum is also removed and the anterior rotator cuff muscles are released, thus exposing the distinct anterior edge of the glenoid. With appropriate commonplace medical imaging software, it is possible to isolate only the bony anatomy from the pre-operative imaging data and produce a virtual 3D model. The program then runs an algorithm that matches the scanned surface of the impression element, with the corresponding anatomy obtained from the processed pre-operative imaging data. Advantageously, the initial pre-operative imaging of the patient can be done before the surgery begins, possibly days or weeks before. Some portion of any impression on the impression element caused by bony anatomy from the surgical field will have a matching topographical area on the pre-operative imaging data. The algorithm identifies these matching sites over as large an area as possible. For the purposes of this embodiment, it is assumed that this process can be externally assisted if, for example, the operator virtually 'colors-in', or otherwise indicates, specific areas on the virtual bony anatomy model, from which they will plan the case, that they are sure will form at least a part of the impression element surface. For example, at the time of surgery, the surgeon can roughly color in these corresponding areas on the molded surface of the impression element with a sterile marker pen. This will assist the algorithm as it will roughly highlight areas that should be near-by each other if it is imagined that the impression element could be brought together with 'virtual' 3D model of the patient's anatomy. 'Registration' algorithms used to co-register data representing a surface configuration with preoperative imaging data are known.

Figure 6:
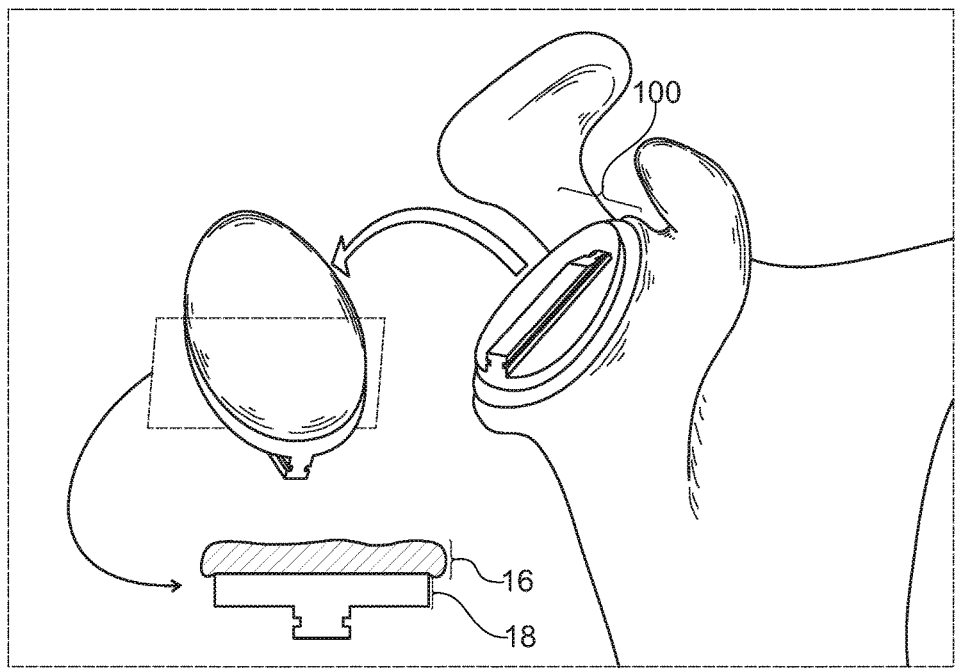
FIG. 6 is a diagrammatic flow chart showing the use of the guide blank of FIG. 2 to take an impression of a surgical site.

Due to the molding procedure of the moldable element, the guide blank can only be fitted back into the surgical field in the same position at which it was first molded as a result of its unique fixed topography. The above algorithm co-registers the impression element with the unique area of anatomy onto which it fits. Through the aforementioned process the impression element has also been co-registered with the carrier, with the guide blank holder, and with the production apparatus. Thus, the guide blank is now precisely positionally defined with respect to the patient anatomy and within the production apparatus. Of course, the positional definition of the impression element or guide blank with respect to the patient anatomy defines the position if the impression element were to be placed back at the surgical site, whereas the position definition with respect to the production apparatus defines the position in the receptor assembly. Put another way, the carrier of the guide blank has been spatially registered with the scanned surface of the impression element but at the same time the impression element has now been registered with the patient anatomy from which it was molded. The result of this process ensures, or at least increases the likelihood, that if, at this point, the guide blank is placed back into the surgical field in the identical position from whence it was molded; the software will 'understand' the spatial orientation and position of the carrier and the impression element with respect to the patient anatomy and be able to generate a 3D 'virtual' model of the guide blank in situ on the bony anatomy as illustrated in FIG. 6.

Guide Creation

In this embodiment, the elements have been set up for the purpose of guiding the orientation and position of the axis through which to place guide wire 12 (FIG. 1) to facilitate the correct positioning of the glenoid component of the total shoulder replacement. As previously described, the production apparatus also houses a modification tool, in this embodiment CNC drill 32 (FIG. 3 and FIG. 4) situated on the opposite end of receptor assembly 28 to 3D scanner assembly 26. CNC drill 32 can, however, be positioned in convenient positions within the production apparatus. Drilling assembly 32 includes motor 50 capable of powering rotating sterile drill bit 48, and apparatus to orientate the position of the drill assembly with respect to the guide blank once the guide blank has been mounted within the guide blank holder within receptor assembly 28.

Motor assembly 50 is provided with an aperture into which can be fitted sterile drill bit 48, sterile drill bit 48 being of diameter just larger than the diameter of selected guide wire 12. The drill can for example be provided with a quick release assembly. The guide blank should remain sterile as it will eventually be placed back into the surgical field. For this reason, when the apparatus is used on a new patient, newly sterilized drill bit 48 is placed into drilling apparatus 32 of the production apparatus before use. The working shaft of drill bit 48 remains sterile as it will not come into contact with other structures other than the sterile guide blank mounted above it.

In this embodiment, drill assembly 32 is capable of translation in the X, Y and Z axes of the plane of scanner 26 while adjustment mechanism 30 is capable, using a second motor, of rotating the affixed guide blank in the X and Y axis. The method described here for the movement of the guide blank and modification tool can be substituted for methods of movement used on existing or future devices such as CNC devices. Both the translational movements of CNC drill 32 and rotation of receptor assembly 28 can be unpowered in a different embodiment. As an alternative to computer controlled positioning, movement can be controlled via the turning of, for example, a graduated dial in order to position and lock a particular axis into a position specified by a computer.

The axis and position through which the surgeon would like to drill into the glenoid cavity to facilitate placement of the glenoid component guide wire is previously specified by the surgeon in the preoperative digital operative prescription or digital plan.

Figure 7:
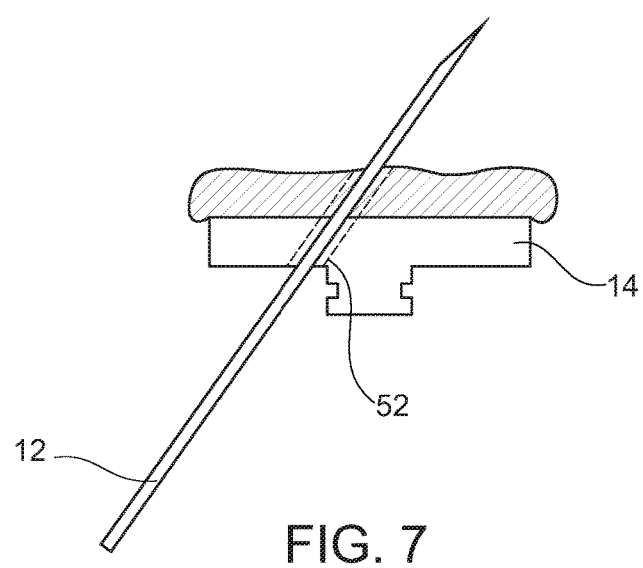
FIG. 7 is a side view showing a guide made from the guide blank of FIG. 2.

Control unit 34 is configured to use the co-registration of the impression element with anatomical features at the surgical site to convert the digital plan into a plan for the impression element. Effectively, the co-registration of the impression element with anatomical features at the surgical site allows the impression element and anatomical features at the surgical site, and therefore the digital plan, to be expressed in the same frame of reference as if the impression element were in place at the surgical site, and thereby allows the digital plan to be converted into a plan for the impression element. The plan for the impression element indicates how the impression element should be modified to form a guide to comply with the digital plan, so that the guide can guide the surgery according to the digital plan when the guide has been placed back into the surgical site from which the original impression was taken. For example, in the embodiments shown in FIGS. 2-7, the plan for the impression element is a plan for hole 52 through the impression element to accommodate guide wire 12, as shown in FIG. 7.

The control unit is also configured to convert the plan for the impression element into modification instructions, the modification instructions being instructions for adjustment mechanism 30 and modification tool 32 in order to modify the guide blank in accordance with the plan for the impression element. The control unit is configured to convert the plan for the impression element into modification instructions using the registration of the impression element with respect to the production apparatus. The control unit can express the impression element, and therefore the plan for the impression element, in the same frame of reference as the production apparatus and can thereby determine modification instructions of how to operate the production apparatus to follow the plan.

The modification instructions provide control instructions to the production apparatus to operate the drilling apparatus and manipulate the position of the guide blank with respect to the drilling apparatus such that a guiding hole can be drilled through the guide blank that satisfies the positional and axial constraints specified in the operative prescription. The aforementioned registration steps ensure, or at least increase the likelihood, that the hole drilled is positionally and axially equivalent to the position of the virtual guide wire with respect to the glenoid from the post-operative plan.

Once the control unit has determined the modification and/or control instructions, it operates the production apparatus in accordance with those instructions to modify the guide blank held in the receptor assembly. The guide blank is now a guide and can be removed from the guide blank holder within the production apparatus cavity and placed back into the glenoid cavity in its fixed position as defined by the now solid impression element. If need be, the guide can be secured in place with some accessory pins, alternatively it can be held in place with applied pressure by the surgeon or an assistant. The surgeon can now drill guide wire 12 through the hole created in the guide as shown in FIG. 7, with the knowledge that the position and orientation at which the guide wire will pass into the glenoid surface will be identical to the pre-operative virtual plan previously specified. Clean passage of the guide wire or surgical drill can be facilitated by previously inserting a suitable sleeve through the prepared hole. Any swarf remaining after the drilling procedure can be washed away before use, alternatively the CNC drill apparatus can be provided with a suction or washer system capable of ensuring no swarf remains at the drilling site.

Once the guide wire insertion process has been completed, the drill can be removed from the end of the fixated guide wire and guide 14 can be slid off the wire, leaving guide wire 12 in place, satisfying the pre-determined positional constraints previously laid out by the surgeon in the operative prescription. At this juncture the procedure can now continue as normal, with the knowledge that the glenoid component will be affixed in the optimal orientation possible as defined by guide wire 12.

Figure 12:
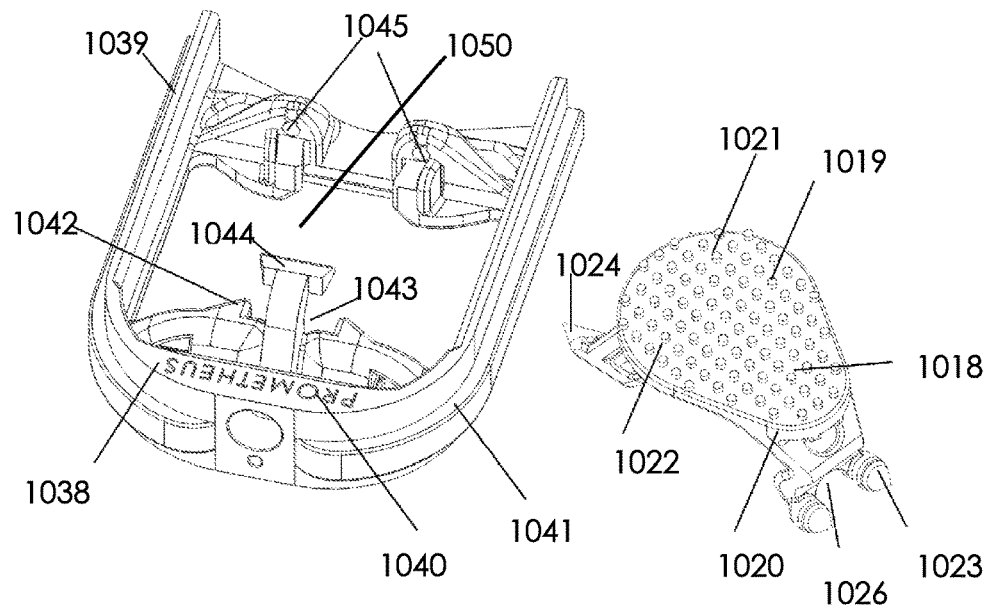
FIG. 12 shows a guide blank holder and a carrier.

FIG. 12 shows guide blank holder 1038 and carrier 1018.

As can be seen, in this embodiment, carrier 1018 includes plateau 1019 which in this embodiment includes narrow region 1020 and wide region 1021, with sides of plateau 1019 tapering from wide region 1021 to narrow region 1020, plateau 1019 having rounded edges.

Plateau 1019 includes a plurality of spikes for receiving and coupling carrier 1018 to moldable material.

Carrier 1018 includes first foot 1023 mounted on plateau 1019 on the opposite surface from spikes 1022 in the region of narrow region 1020, and second and third feet 1024, 1025 mounted on the opposite surface of plateau 1019 from spikes 1022 in the region of wide region 1021.

The first, second and third feet are mounted to legs which depend from the plateau. First foot 1023 includes a capture element including first and second protrusions joined by wall 1026 which extends only part the way along the protrusions, so that the protrusions for part of their length are joined by wall 1026, and for part of their length have a gap between them.

Guide blank holder 1038 includes perimeter wall 1039 which extends substantially straight along lateral walls and includes curved front wall 1040 but has an open back, top, and bottom. Lip 1041 extends outwardly from a base of perimeter wall 1039.

First retaining element 1042 is attached to the perimeter wall adjacent to front wall 1040. First retaining element 1042 includes recess 1043 into which the first and second protrusions of first foot 1023 of carrier 1018 can be placed and obstruction element 1044 arranged adjacent to recess 1043 to obstruct wall 1026 of carrier 1018 when foot 1023 of carrier 1018 is in recess 1043. Recess 1043 is bordered by a wall. This wall has an opening facing obstruction element 1044.

Guide blank holder 1038 also includes first and second food rests 1045 disposed so that second and third feet 1024, 1025 of carrier 1018 can rest upon them when first foot 1023 of carrier 1018 is coupled with retaining element 1042. First and second foot rests 1045 are positioned adjacent to the open back end of guide blank holder 1038.

When carrier 1018 is to be inserted into guide blank holder 1038, first foot 1023 is placed into retaining element 1042 so that the first and second protrusions are disposed in recess 1043 and retained therein on three sides by the wall of the recess. Carrier 1018 is prevented, or at least deterred, from leaving recess 1043 via the opening in the recess owing to the obstruction of movement of wall 1026 by obstruction element 1044.

The second and third feet of carrier 1018 rest upon foot rests 1045. The carrier is then held in receiving zone 1050 in the guide blank holder, protected by perimeter wall 1039.

Figure 13:
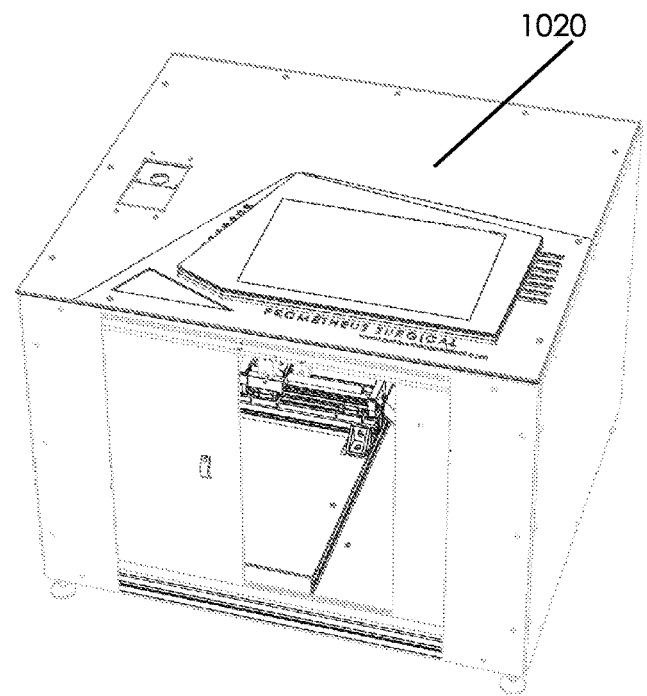
FIG. 13 shows a production apparatus.

When placed into production apparatus 1020 such as shown in FIG. 13, lip 1041 of guide blank holder 1038 couples with a channel in receptor assembly 1028 of the production apparatus in a predetermined position without the carrier coining into contact with the production apparatus.

Figure 14:
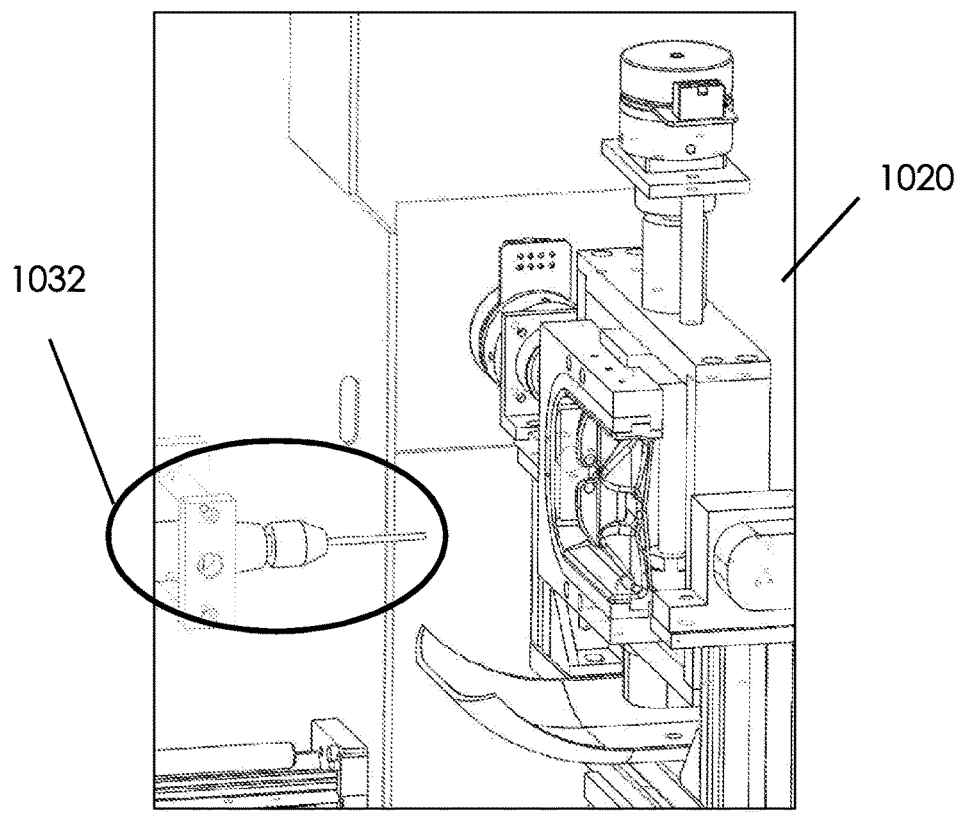
FIG. 14 shows an internal view of the production apparatus of FIG. 13.
Figure 15:
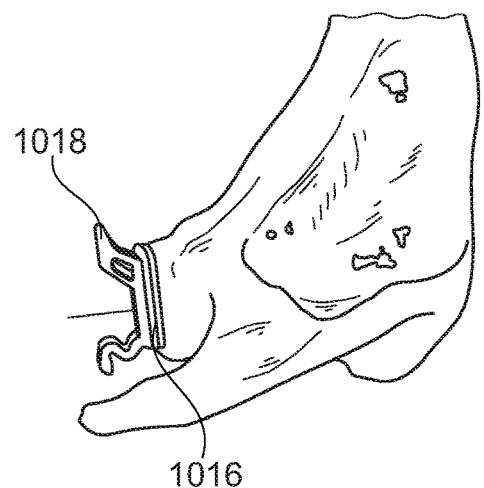
FIG. 15 shows the carrier of FIG. 12 with a moldable element in place on a model of a scapula.
Figure 16:
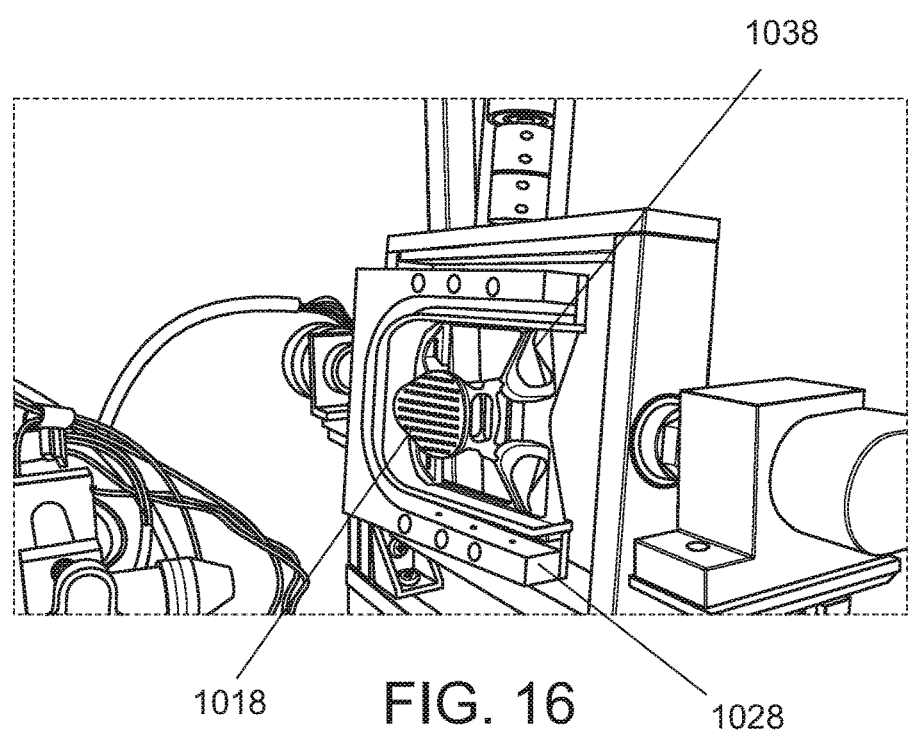
FIG. 16 shows the guide blank holder and carrier of FIG. 12 in the receptor assembly of the production apparatus of FIGS. 13 to 15.
Figure 17:
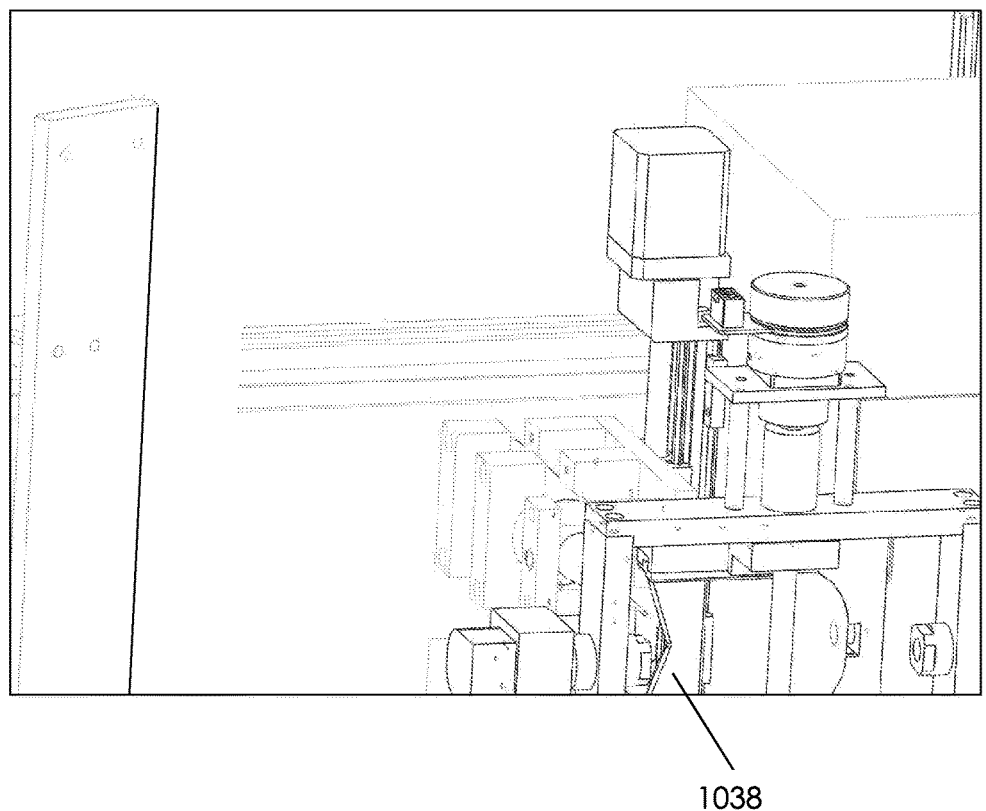
FIG. 17 shows another view of the arrangement of FIG. 16.

FIG. 14 shows modification tool 1032 in production apparatus 1020.

The embodiment of FIG. 12 is particularly advantageous as the carrier can be clipped into the guide blank holder with one hand.

The processing or software described herein, such as the registration of elements, and the calculation of modification instructions, can be performed by control unit 34 itself or can be performed by an external computer.

The above described embodiments provide a method specifically for the placement of a guide wire into the glenoid cavity during the TSA procedure.

Figure 8:
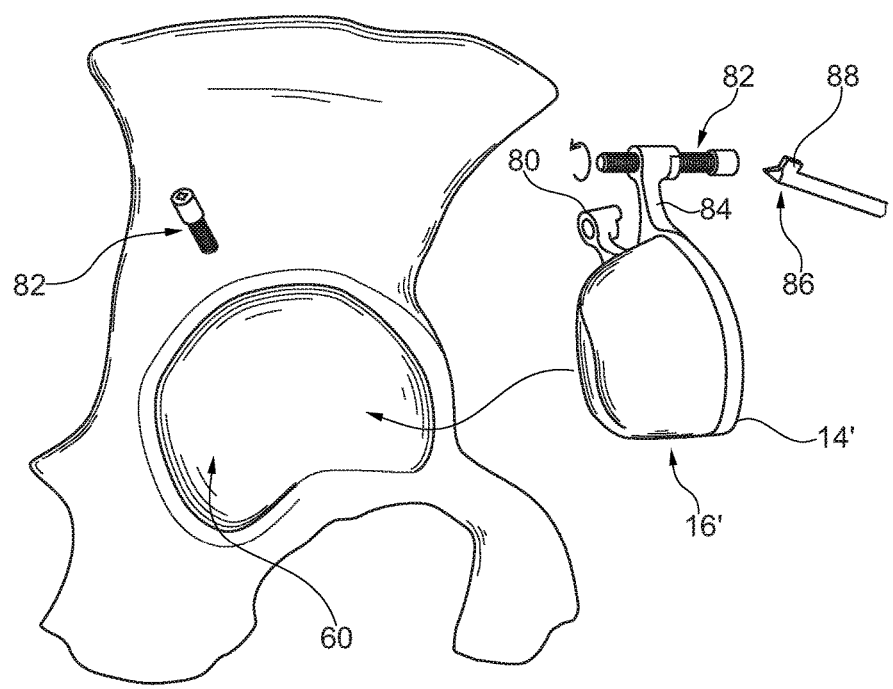
FIG. 8 shows a guide blank according to another embodiment being placed against a surgical site.

Other embodiments can be used for other surgical procedures. Embodiments of the guide can be produced such that they are specifically designed for certain procedures. An example might be a guide designed to facilitate the positioning and orientation of the acetabular component in total hip arthroplasty surgery as shown in FIG. 8. In this embodiment, impression element 16' of guide 14' is produced such that it is bulbous in structure similar to that of the femoral head, so as to support the moldable material, and to minimize, or at least reduce, the amount of material needed.

A range of sterile, pre-packaged guide blanks can be provided reflecting the various sizes of acetabulum that can be presented.

Once moldable element 16' has been activated, the guide blank can be pressed into acetabulum 60, ensuring that moldable element 16' conforms to the unique topography of the intraoperatively exposed bone. Once moldable element 16' has been modified in this way, the process can continue in the manner described in the previous embodiment in order to produce a guide.

The production apparatus can be designed such that it will accommodate guide blanks of differing types reflecting the different types of operation in which they might be used. All guide blanks might have an identical standardized carrier where practical. The moldable element will vary in initial design and size to accommodate differing applications.

Embedded RFID tags, bar, or QR codes can identify various aspects of the patient and procedure, such as patient name, operation side, digital plan, and component sizing to the software.

Figure 9A:
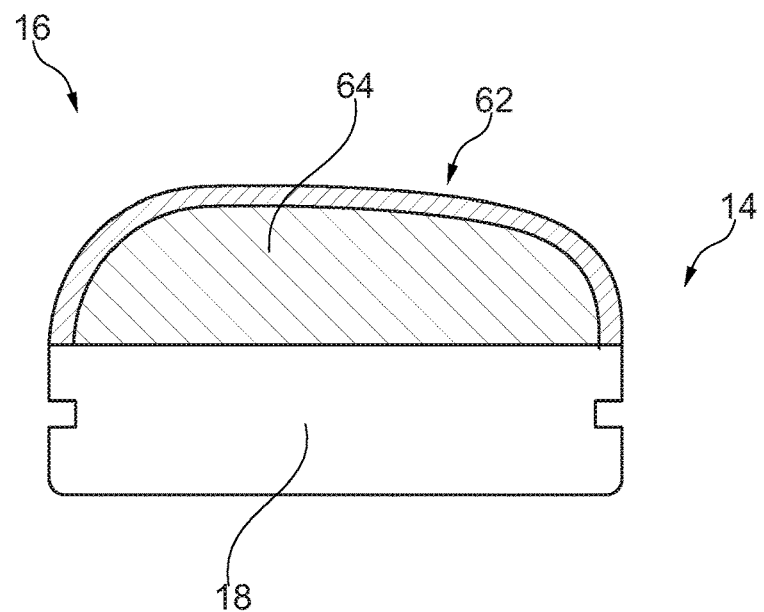
FIG. 9A shows a guide blank.

The following describes one design for the moldable element of the guide blank, although other designs and materials can be used in other embodiments. Moldable element includes two constituent parts and is shown in FIG. 9A. Outer layer 62 that will come into contact with patient anatomy includes a low temperature thermoplastic. Layer 64 immediately below outer layer 62 is formed from a permanently deformable material with a consistency suitable to provide mechanical support to outermost thermoplastic layer 62. This material is pre-formed in a configuration such that that it can fit the general shape of the anatomical area to which the guide blank is designed to be molded. This dictates the general shape of the as yet unformed thermoplastic layer 62. Moldable element 16 is mounted on carrier 18 of guide blank 14.

Figure 9B:
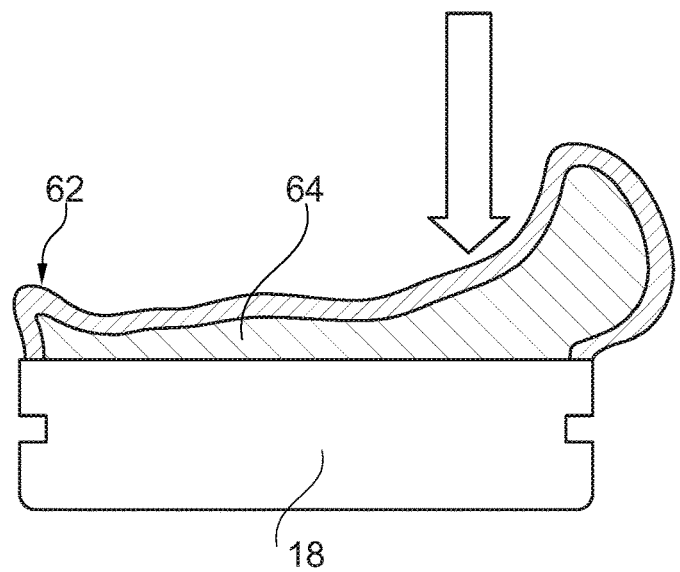
FIG. 9B shows the guide blank of FIG. 9A subject to a deforming force.

To activate guide blank 14, an infrared heated receptacle can be provided associated with or as part of the production apparatus. The selected guide blank can be placed into the aforementioned receptacle and the thermoplastic surface heated to its transition temperature. At this point, the production apparatus can set itself up to shortly receive the molded guide blank, for example, by selecting the correct tool from an internal library for the imminent modification of the prepared guide blank. The thermoplastic that is selected for outer layer 62 has a transition temperature lower than that of the tissue damaging threshold. Once sufficiently heated the guide blank is held by the carrier and the moldable element is pressed onto the anatomical area of interest thus allowing thermoplastic layer 62, supported by deformable material layer 64 underneath, to take the shape of the underlying anatomy before, once again, becoming solid as shown in FIG. 9B.

Figure 10:
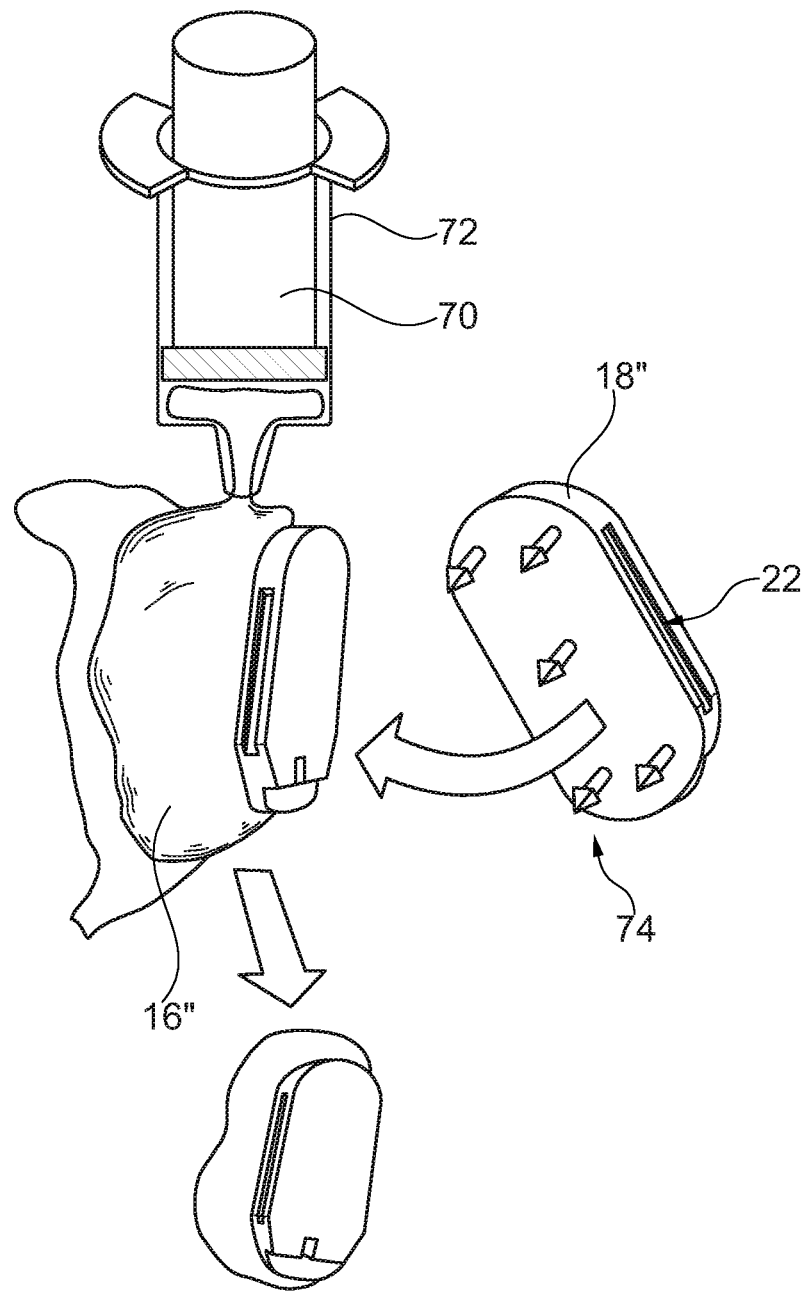
FIG. 10 shows the production of a guide blank according to another embodiment.
Figure 11:
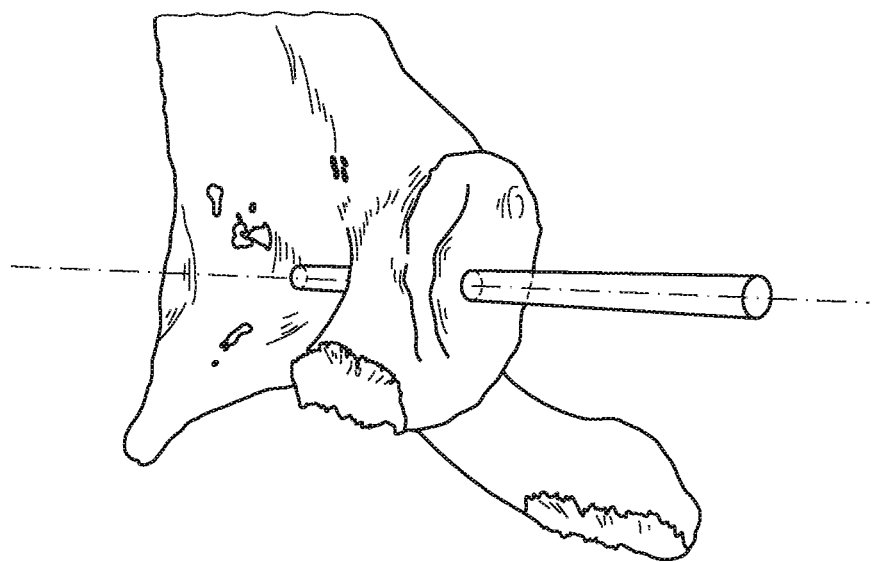
FIG. 11 shows a surgical plan being constructed.

In another embodiment, moldable element 16" and carrier 18" begin the process as separate entities as shown in FIG. 10. A sterile biocompatible, rapid setting polymer 70 is provided in sterile syringe 72. Carrier 18" has features 22 that allow it to be slotted into the aforementioned guide blank holder and on its reverse surface it possess barbed members 74 that generate adhesive forces if the member is pressed into rapid setting polymer 70. The surgeon injects polymer 70 onto the surface of the dissected joint or bony anatomy and can roughly shape it into a globular body. Sterile carrier 18" is then pressed into the globular body as it sets hard such that the barbed surface of carrier 18" will end up solidly held in the body of the polymer so that the globular body forms moldable element 16". The guide blank holder interfacing surface of the carrier remains exposed. In this way, once fully set, this guide blank can be removed from the surgical field and will include a body of solid polymer that has been molded to the topography of the chosen bony anatomy and a carrier geometrically fixed in position with respect to the molded surface. From this point, the process can now continue in the same manner as has been previously described.

In a further embodiment, the guide blank can consist solely of a body of moldable material without a carrier. The moldable material in such an embodiment is sterile and able to 'set' to become hardened. A sterile guide blank holder is provided with, for example, spiked hinged members such that the now set body of moldable material is able to be securely fastened into the guide blank holder. As there is no carrier in this case the body is affixed into the guide blank holder such that its molded face is in view of the scanner. The body is now fixed with respect to the guide blank holder which is itself geometrically fixed with respect to the rest of the production apparatus. The scanner now scans the surface of the body thus geometrically registering it with both the preoperative CT scan and the production apparatus. The body can now be modified in the above described manner and placed back into the patient to act as a guide.

The guide blank can be modified such that it is capable of guiding a multitude of different surgical processes. Modifications might include holes for guide wires as described above, but can include other guidance or navigational structures. Options might include slots to cut grooves or section pieces of bone in operations such as the total knee replacement or to dictate angle and position for the removal of the proximal humeral head in TSA surgery.

Figure 18:
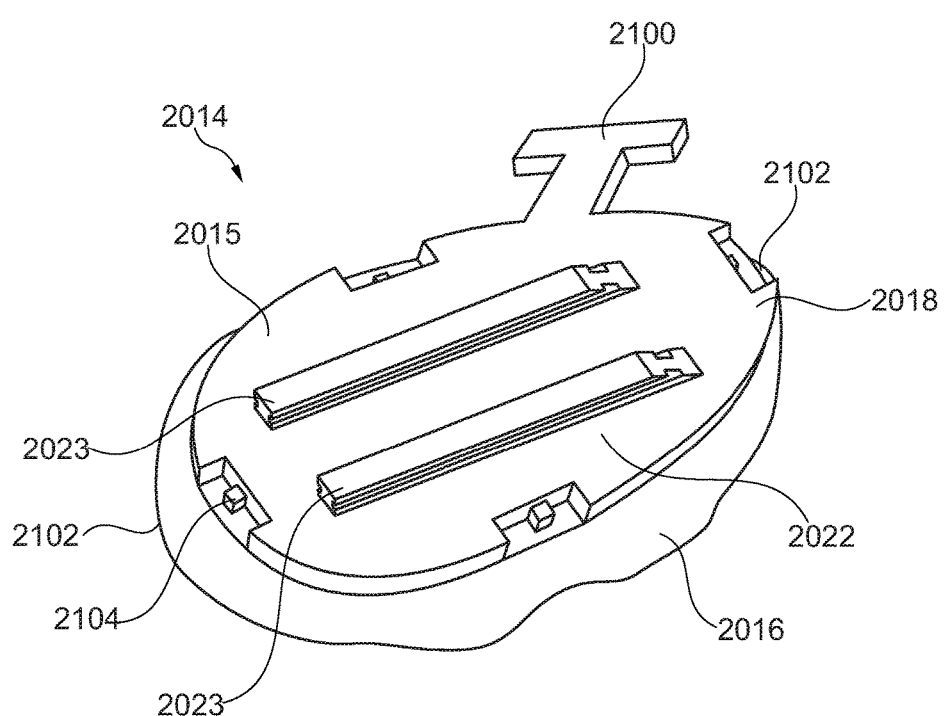
FIG. 18 shows a carrier.
Figure 19:
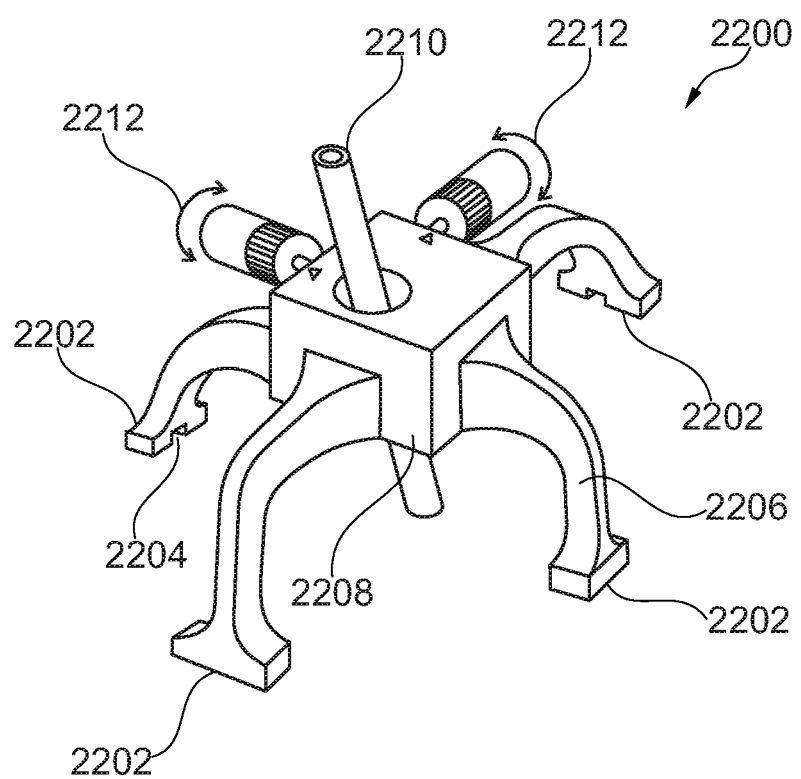
FIG. 19 shows a guiding element.

Another embodiment is shown in FIGS. 18 and 19. FIG. 18 shows guide blank 2014 corresponding in many respects to the guide blank shown in FIGS. 2-7. Carrier 2018 includes a coupling arrangement including guides in the form of channels 2022 similar the embodiments shown in FIGS. 2-7. In this embodiment, channels 2022 are provided on first and second rails 2023 which are part of the surface of carrier 2018. However, channels 2022 work in substantially the same way as channels 22 described above.

Carrier 2018 has a predetermined configuration and is rigid so as to maintain that predetermined configuration during molding of the moldable element and scanning.

In this embodiment, carrier 2018 includes a reference element or fiducial marker 2100 in the form of a T-shaped lateral projection from carrier 2018. As with other embodiments, in this embodiment, carrier 2018 is arranged opposite a surface of moldable element 2016 which will be scanned. Fiducial element 2100 is configured to project laterally beyond moldable element 2016 so that a scan of the surface of the moldable element opposite carrier 2018 will include a scan of fiducial element 2100. With knowledge of the configuration and position of the fiducial element with respect to body 2015 of the carrier, the position of carrier 2018 as a whole with respect to moldable element 2016 can be obtained from the relative position in the scan of fiducial element 2100.

In this embodiment, carrier 2018 includes a guiding element coupling arrangement for coupling carrier 2018 to a guiding element. In this embodiment, the guiding element is sterile programmable tool 2200 as shown in FIG. 19. However, in other embodiments, the guiding element can be other elements for guiding a surgical component to interact with a patient.

In this embodiment, the guiding element coupling arrangement includes a plurality of recesses 2102 for receiving respective feet 2202 of guiding element 2200. In this embodiment, there are four recesses for four feet of the guiding element as this provides a stable coupling. However, a different number can be included in other embodiments.

Each of recesses 2102 includes alignment block 2104 to be received in alignment recess 2204 of the respective guiding element foot in order to maintain the guiding element, or at least those parts of the guiding element that are fixed with respect to feet 2202, in a desired predetermined position with respect to carrier 2018. As is described below, some components of the guiding element can be movable for example to allow the guiding element to be placed into one of a plurality of different configurations.

As shown in FIG. 19, guiding element 2200 includes four feet 2202 to couple with four recesses 2102 on carrier 2018. Each of feet 2202 is coupled to leg 2206 which depends from body 2208 of guiding element 2200. In this embodiment, the body and feet are fixed with respect to each other. The body of the guiding element includes tool guide 2210 which can be positioned in one of a plurality of configurations. In other words, it is programmable. In this embodiment, tool guide 2210 is a drill guidance tube which passes through body 2208 of guiding element 2200. In other embodiments, tool guide 2210 can be a guide for different types of tools, for example can include a reconfigurable slot through which a cutting tool can operate.

In this embodiment, guiding element 2200 includes first and second dials 2212 to orientate tool guide 2210 in two mutually perpendicular axes in order to position tool guide 2210 in a desired one of the plurality of possible configurations. These dials 2212 are designed to be adjusted by the surgeon by hand. In other embodiments, tool guide 2210 can be automatically reconfigured.

In some embodiments, guiding element 2200 can include a surgical tool to be guided by tool guide 2210 and in other embodiments tool guide 2210 can be for guiding a separate tool.

In operation, moldable element 2016 becomes an impression element providing an impression of a surgical site in the same manner as described above. The impression element is scanned and registered with anatomical features of the patient's anatomy by software, again as described above. However, in this embodiment, because of guiding element 2200 it is not necessary to modify the impression element and carrier in order to form a surgical guide. In this embodiment, impression element 2016 is registered with carrier 2018 using the presence of fiducial element 2100 in the scan of impression element 2016. As described above, from the position of fiducial element 2100 in the scan, the position of part of, if not the entire, carrier 2018 with respect to the scan can be determined, and carrier 2018 as a whole can be registered to impression element 2016. It is therefore not necessary in this embodiment for the carrier to be clipped into a production or registration apparatus, since the registration is performed from one scan. A surgeon or a surgeon's assistant simply scans the impression element and fiducial element, for example by a handheld 3D optical scanner.

On an electronic level, what is happening is that data representing the configuration of carrier 2018 is registered with surface data from the scan representing the surface configuration of impression element 2016.

Once carrier 2018 has been registered with impression element 2016, guiding element 2200 can be registered with impression element 2016. In other words, data representing the structure of the guiding element can be registered with the surface data representing the configuration of the surface of impression element 2016. The data representing the structure of the guiding element can include data representing a predetermined configuration with respect to carrier 2018 of those parts of guiding element 2200 which are fixed with respect to the carrier after coupling and data representing the configurability of the reconfigurable parts of the guiding element. In other embodiments, the data representing the structure of the guiding element can include data representing each of the possible configurations of the guiding element with respect to the carrier after coupling. The data representing the structure of the guiding element can be registered with the surface data using the registration of carrier 2018 with impression element 2016.

Guiding element 2200 can then be registered with anatomical features of the patient's anatomy. In other words, the data representing the structure of guiding element 2200 can be registered with features of image data representing features of the patient's anatomy, for example from pre-operative imaging data. This can be done using the registration of guiding element 2200 with impression element 2016, and the registration of impression element 2016 with the anatomical features of the patient.

With guiding element 2200 registered with anatomical features of the patient, the software determines a desired configuration of tool guide 2210 in order to guide a tool to form a surgical interaction with a patient which is in accordance with the surgical plan.

In this embodiment, body 2208 of the programmable tool is inherently registered with carrier 2018 as it is only able to be clipped in in one way. Impression element 2016 is registered to patient anatomy in the manner discussed above. The impression element is then registered to carrier element 2018 using the fiducial marker. Impression element 2016 is now inherently registered with body 2208 of the programmable tool by virtue of the fact they are both registered to carrier 2018. As described above, once anatomical registration has been carried out, the digital plan can now be expressed in the frame of reference of impression element 2016 and carrier 2018 and, as previously, be used to create a modification plan. In this embodiment, programmable tool body 2208 is registered with respect to the impression element and the carrier so the digital plan can now be expressed in the same frame of reference as programmable tool body 2208. The computer software is pre-programmed with an inherent 'knowledge' of the dynamics of tool guide 2210 with respect to tool body 2208 as facilitated by programming dials 2212, thus, the software can now calculate an appropriate configuration or transformation such that tool guide 2210 axis and position is identical to the axis and position of the axis of the digital plan. It is to be noted that this axis can also be described with respect to the impression element or carrier 2018. Once anatomical registration has been carried out, the coordinates describing the geometry of the digital plan with respect to the patient anatomy can also be described with respect to the impression element and carrier.

The software now converts this configuration or transformation into the numerical values to which programmable tool control dials 2212 are rotated such that tool guide 2210 matches the axis and placement of the appropriate drilling axis in the real world. A surgeon or assistant can now rotate the dials to the appropriate value. This ensures, or at least increases the likelihood that, the programmable tool is clipped onto carrier 2018 in appropriate recessions 2102 and the surgeon drills through tool guide 2210 into the patient anatomy (in this embodiment passing through the carrier and impression element) thus placing a guide wire or pin in the identical geometrical configuration as defined by the plan.

This embodiment therefore has the advantage that it does not require a production apparatus, and does not require direct modification of the impression element, but can use a standardized programmable tool and register most, if not all, the components together using a simple handheld scanner.

The embodiment of FIGS. 18 and 19 can be provided without fiducial element 2100, and the registration can be performed in a registration apparatus that corresponds in many respects to the production apparatus described above; however, the production apparatus in such an embodiment does not need a modification tool.

In some embodiments, guide element 2200 can be an integral part of carrier 2018. Furthermore, the guide element does not need to be programmable, but can be provided in a fixed predetermined location with respect to carrier 2018 to allow a reference marker to be attached to a patient's anatomy for guidance or navigation for further surgery. For example, in FIG. 8, the carrier can include holes 80 in arms 84 or other extending members for the placement and registration of guide pins or screws 82 that can, themselves, orientate other surgical equipment. Carrier 14' is registered with anatomical features of the patient in the manner described above. Since holes 80 and arms 84 are in a predetermined position with respect to the body of the carrier, they are therefore also registered with the anatomical features of the patient. The standard hole in carrier 80 defines the axial position of the screw or pin and associated flanged screw driver 86 can drive the screw into the bone until flange 88 comes into contact with the top of guidance hole 80, thus limiting the distance that the screw or pin can be driven into the bone. Once these guide pins 82 are in place, separate apparatus can be placed over the pins such that it will also be inherently registered to patient anatomy and the original guide can be discarded. This process allows the joint surface to be fully exposed while intraoperative guidance can still be used as the fixed members screwed into nearby bone will be registered to patient anatomy. In this manner, standardized surgical guides can be positioned in a patient specific manner thus allowing the precise placement of standardized cuts or holes in, for example, a knee replacement procedure.

Figure 20:
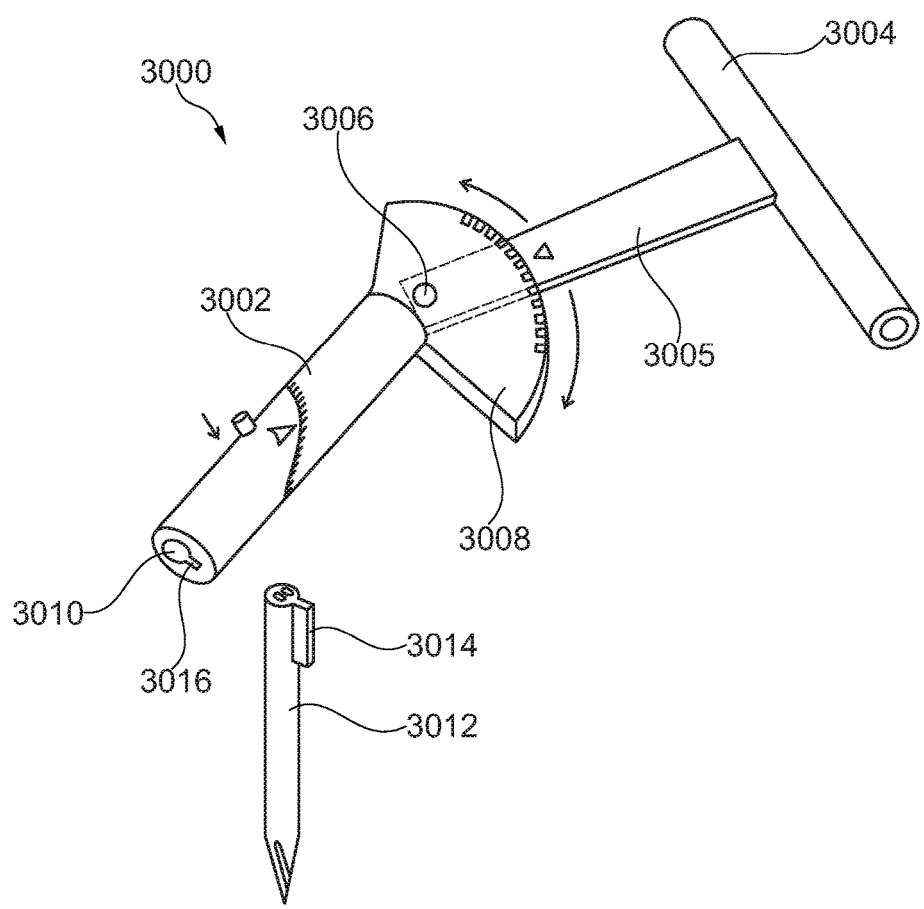
FIG. 20 shows a guiding element.

FIG. 20 shows an example of such separate apparatus that can be placed over the pins so that it will be inherently registered to anatomical features of the patient's anatomy.

FIG. 20 shows programmable guiding element 3000 including pin sleeve 3002 and tool guide 3004. Tool guide 3004 can be positioned in one of a plurality of positions with respect to pin sleeve 3002. In this embodiment, tool guide 3004 is a drill guide, however in other embodiments other tool guides can be provided.

In this embodiment, tool guide 3004 is mounted on a stalk which is coupled to pin sleeve 3002 by ratcheted pivot mechanism 3006 which allows stalk 3005 to be positioned at one of a plurality of angles with respect to pivot 3006. In this embodiment ratcheted pivot 3006 includes dial 3008 marked with positions such as angles so that the surgeon can position stalk 3005 at the desired angle.

The ratcheted pivot 3006 does not need to be ratcheted in every embodiment, but it is provided with a means to hold the stalk in a desired position.

In addition, pin sleeve 3002 includes first and second mutually twistable components and markings to show the extent of twist. Accordingly, in this embodiment, by appropriate twisting of the pin sleeve and movement of the stalk, tool guide 3004 can be placed in a plurality of different configurations, each configuration providing the tool guide in a different position with respect to a pin in the pin sleeve.

Pin sleeve 3002 includes internal passage 3010 for receiving a pin such as pin 3012 shown in FIG. 20. In this embodiment, passage 3010 and pin 3012 are asymmetric so that pin sleeve 3012 will only fit over pin 3012 in one orientation, thereby ensuring that guiding element 3000 is positioned on pin 3012 in a known predetermined manner. In this embodiment, this is achieved by pin 3012 including flange 3014 and passage 3010 including corresponding channel 3016 for receiving flange 3014. However, in another embodiment, a carrier can be designed similar to the depiction in FIG. 8 however it will guide the placement of two planar pins. In this way, flanged pins need not be used as a programmable object possessing two pin sleeves can be used and slid over both pins thus locking the body both positionally and axially.

In use, once the carrier and impression element of FIG. 8 have been used to position a pin such as pin 3012 in a known position and configuration with respect to anatomical features of the patient's anatomy, pin sleeve 3002 of guiding element 3000 is positioned over pin 3012. Owing to the predetermined structure and adjustability of guiding element 3000, or the pre-calibrated possible configurations of guiding element 3000, guiding element 3000 can thereby be registered to the anatomical features of the patient's anatomy using the registration of pin 3012 to the anatomical features of the patient's anatomy. Guiding element 3000 can therefore be expressed in the same frame of reference as anatomical features of the patient's anatomy and therefore the same frame of reference as the surgical plan. The desired configuration of guiding element 3000, that is to say the desired position of tool guide 3004, or in this embodiment the desired settings for the ratcheted pivot and mutually twistable components in order to enable a surgical interaction with a patient in accordance with the surgical plan can thereby be determined.

The software outputs the desired configuration following the anatomical registration of the impression element and carrier 14' that has allowed the placement of a pin(s) into known locations on patient anatomy. The software will know the locations of these pins thus can output the correct configuration of the tool 3000 such that it can be modified by surgical staff and placed over the pins in a known way. The tool guidance element 3004 can now be drilled through, entering the patient anatomy in a known way according to the surgical plan.

In some embodiments, a programmable tool can be registered to patient anatomy exclusively using an impression element without a carrier. A digital or surgical plan is created based on patient imaging data. In theatre, the surgical site is exposed and the surgeon can place a guidance pin or screw at a location of their choosing such as pin 3012 depicted in FIG. 20 that possesses a known orientating factor such as flange 3014. Alternatively, the surgeon can use a separate tool to place two parallel pins in such a configuration that the standard part of programmable tool 3010 can be slid over the top thus ensuring a known planar orientation.

These pins can be registered with patient anatomy so that a programmable tool can be appropriately modified and affixed to the pins such that its tool guidance feature 3004 is correctly positioned according to the surgical plan.

Once the pin(s) are placed, a globular portion of sterile moldable material can be molded onto the surgical site ensuring that the pins pass through the globular body of material as it sets. When solidified, the globular body can be separated from the surgical site and slid off the pins retaining a surface impression of the surgical site studded with the holes left by the pins that can or cannot pass all the way through the globular body.

Once remote from the surgical site, fresh sterile pins, or markers in the same shape as the pins in the surgical site, can now be placed back into the holes in the globular body such that they protrude out from the surface possessing the impression from the surgical site. This arrangement can now be held in front of, for example, a 3D optical scanner and scanned creating a 3D surface model. This 3D model will comprise the impression of the surgical site and the pins or markers extending from the impression surface. In computer software, a surgeon can now select the pin(s) or marker(s) on the computer model so that the software can differentiate between the impression surface and the markers. The software can now use the impression element surface and carry out an anatomical registration in the above way. The axis and position of the pin(s) marker(s) are inherently registered with the impression element as they are in the same 3D scan thus once the impression element is registered to patient anatomy in the normal way, the axis and position of the pin(s) marker(s) can also be expressed in the same reference frame as the patient anatomy. In this way, the physical pin(s) and marker(s) are now registered with respect to patient anatomy. As described previously, the computer software can now calculate an appropriate configuration or modification to be made to a programmable tool such that it can be slid over the original pin(s) in situ in the surgical site and used to carry out a surgical intervention on the patient.

A surgical pin can be designed with a specifically patterned head that can leave an impression in the impression element. In this embodiment, the scanner would scan the impression element producing a model comprising the surgical site impression as well as the impression of the patterned head of the pin. This pattern can be picked up by software and used to register the location of the pin with respect to the impression element surface and subsequently to the patient anatomy. A programmable object can be attached to the head of this pin in a known way thus, after appropriate modification, it can be used to guide a tool in the above way.

Utility in Surgical Navigation

The herein described guide is solely limited to the guidance of surgical tools. Surgical navigation has utility in a number of different surgical fields and yet the majority of prior art functions with registration techniques that rely on optical registration methods or require the surgeon to touch pre-determined areas of anatomy with a digitizer arm. These methods are laborious and time consuming and often require complex and costly equipment. In many situations this approach is impractical, for example, in compact operative fields where soft tissue can obscure the view and the necessary bulky apparatus can be cumbersome and increase the operation time.

The above described elements can be used to overcome these problems. A guide can be provided with the intended function of orienting a 'standard marker' that will be drilled into the patient's bony anatomy. This marker can be registered with the pre-operative imaging data and patients anatomy utilizing the method disclosed above. The guide can be removed from the surgical site and discarded leaving behind a 'standard marker' fixed to the bony anatomy. The usual navigation techniques can now be employed such as optical tracking of the 'standard marker' thus allowing conventional navigation techniques to be used. The advantage to this approach is that the optical system can now be focused onto the fixed marker which can be away from the surgical site.

In some embodiments in which an impression element is modified by a modification tool, as well as defining the orientation and axial position of a guide wire, pin or similar orthopaedic hardware, the guide can be modified such that a depth to drill can be defined. This can be explained in the following embodiment with respect to the TSA. A surgeon will not want to penetrate the anterior wall of the scapulae while drilling a guide wire into the glenoid cavity. While the aforementioned processes are capable of guiding the axial position and orientation of the wire placement, it cannot define the depth the wire is placed into the glenoid. This problem can be overcome with the use of a stepped hole. First, a wire guidance hole will be drilled through the guide blank. A second drill bit will now be employed of a greater diameter. This will drill along the same axis and in the same position as the first hole however it will not travel the full length of the guide blank. This process will produce a stepped shoulder within the original guide hole. Once the guide is placed back into the surgical field, the surgeon can now drill through the guide with a suitable guide wire featuring a corresponding 'step' in its design to correspond with the internal 'step' within the guide hole through the guide. In planning the position of the 'step', the microprocessor of the production apparatus is pre-programmed with information regarding the location of the 'step' on the shaft of the drill bit used by the surgeon. With this information, it can calculate the depth to drill the greater diameter hole through the guide blank to thus define the depth the guide wire can be placed as the surgeon will be prevented, or at least deterred, from drilling further than the stepped shoulder allows. Alternatively, the processor can specify the position on the shaft of the guide wire to place a lockable cuff in order to specify a specific depth. This position is calculable due to the generated geometric knowledge of the impression element of the guide blank with respect to the carrier and the required depth to be drilled as defined in the surgical prescription.

In some embodiments, a guide blank can be provided possessing certain modifications to the carrier in the form of fixed members or markers, which can be considered to be fiducial markers extending out such that when the impression element surface is viewed by a 3D scanner, the fixed members of the carrier are also visible in the scan. As a result of this, the scanning process generates a digital 3D model of the impression element surface (as described above). This model can also possess 3D geometric data of the fixed members. The members are inherently geometrically fixed with respect to the carrier thus when the impression element is scanned in the same reference frame as these members, the impression element can be spatially registered with respect to the carrier. The device processor is programmed to create a virtual model of the position of the impression element with respect to the carrier by registering the fixed members of a 'blank' model of a carrier with the 3D image of the members from the scanned guide blank.

This embodiment allows for the 3D scanning components and the, for example CNC, modification components of the aforementioned production apparatus to be split into separate assemblies. For example, an operator can now take a mold of the joint surface in the described manner with a guide blank including fiducial markers. Once hardened, the guide blank is removed from the joint surface and held, possibly simply in the surgeon's hand, with the molded impression element facing a 3D scanner that might be held by a non-sterile assistant or positioned on a stand on a separate table. The guide blank is optically 3D scanned producing a 3D digital model comprising the molded impression element surface and the optically visible fixed members extending from the carrier. This 3D model is sent to a processor where the surface of the impression element can be registered with patient anatomy and hence the operative prescription in the same manner as described in other embodiments. The processor also registers the molded impression element surface with respect to the carrier due to the presence of the members in the 3D model generated by the 3D scanner. Once registration is complete, the guide blank can now be clipped into the guide blank receptor assembly of a production apparatus consisting solely of the receptor assembly and a modification tool, such as a CNC drill, cutter or marker such as the configurations described above. In a similar manner to that described above, as a result of the fixed geometry of the carrier, it is only possible to affix the guide blank into the production apparatus in a known position. The contours of the impression element are spatially registered with the carrier therefore they are also inherently spatially registered with the modification tool in the production apparatus through the standardized, carrier mediated fixation method. As a result, the modification tool can drill, cut or mark the guide blank in such a way that when a tool is subsequently passed through the resulting guidance channels its path satisfies the constraints of the pre-operative prescription.

In other words, as described above, the guide blank does not necessarily have to have a carrier. The scanner, or rather the control unit, 'knows' the location of items within the production apparatus so that if a molded lump of impression material is solidly fixed into the production apparatus, the scanner can scan the molded section and inherently register it to other items within the production apparatus so that it can be appropriately modified.

In addition, by providing a fiducial marker on the carrier that is scanned along with the impression element, it is not necessary to have the scanner and modification tool in the same apparatus.

In some embodiments, instead of a modification tool, a modification guide is provided in the production apparatus. This works in substantially the same way as the modification tool, except that it is simply positioned in a desired location with respect to the guide blank to guide a separate external tool to modify the guide blank in the desired manner.

It is possible to use a surface configuration recorder to produce surface data representing a surface configuration. In the embodiments above, the surface data is obtained using a scanner. However, in some embodiments, it is possible to use a digitizer arm which can be touched on a plurality of points on the impression element surface.

All optional and preferred features and modifications of the described embodiments and dependent claims are usable in the various taught herein. Furthermore, the individual features of the dependent claims, as well as all optional and preferred features and modifications of the described embodiments are combinable and interchangeable with one another.

Embodiments can be provided in accordance with the following clauses:

A method for the intraoperative production of a surgical guide, jig or navigation tool utilizing pre-operative imaging data.

An apparatus for the intraoperative modification of a jig to a planned geometry such that it can be fitted to the patient and used to guide cutting/drilling intra-operatively An apparatus for the local intraoperative modification of a jig that has been fitted to a patient intra-operatively, modification to take place according to 3D digital planning data An apparatus for the local intraoperative modification of a jig that has been fitted to a patient intra-operatively, modification to take place according to 3D digital planning data, said apparatus incorporating a work chamber wherein the modification of the jig takes place, said chamber can be dressed with sterile protective sheets, enclosures or bespoke lining materials such that the process of adaptation can take place in a sterile micro-environment.

A CNC or other variety of digital/programmable cutting or drilling apparatus for the local intraoperative modification of a jig that has been fitted to the patient intra-operatively, modification to take place according to 3D digital planning data, as described in previous clauses.

An apparatus for the intraoperative modification of a jig that has been fitted to the patient intra-operatively, modification to take place according to digital 3D planning data, following co registration of preoperatively acquired digital data with 3D data obtained at the time of operation.

A jig for use with the apparatus described in previous clauses, where the jig incorporates a prefabricated element that provides a frame of reference for digital planning and modification, and permits fixation to said apparatus.

A jig which is in part formed from a moldable material, e.g. a silicone impression material or a thermoplastic material, which is used to form the tissue fitting surface of the jig together with a rigid, standardized tray to carry said material.

An apparatus equipped with, or associated with a scanner capable of scanning the moldable element of the jig to acquire 3D data to allow registration of the jig with preoperative scan data.

A jig for use in computer assisted orthopaedic surgery, where said jig is assembled from a moldable material, e.g. a silicone impression material which is used to form the tissue fitting surface of the jig and a rigid tray to carry said material, wherein the tray itself provides a frame of reference for digital planning, and modification.

A jig which is assembled from a moldable material, e.g. a silicone impression material which is used to form the tissue fitting surface of the jig and a rigid tray to carry said material, wherein the tray itself provides a frame of reference for digital planning and modification, also incorporating elements that facilitate connection to an apparatus capable of modifying the jig according to digital planning data A device as in previous clauses where a jig is assembled from a moldable material, e.g. a silicone impression material which is used to form the tissue fitting surface of the jig and a rigid tray to carry said material, wherein the tray itself provides a frame of reference for digital planning, and modification, and incorporates elements that facilitate connection to an apparatus capable of rapidly modifying the jig in a localized sterile enclosure, according to digital planning data A method for the co-registration of patient surgical anatomy with pre-operative or intraoperative imaging data, where one dataset is acquired from that of the 3D surface of a moldable material, intraoperatively molded to the topography of exposed patient anatomy.

A jig with both a temporarily modifiable component and a standardized component, such that it can be located into position by the use of an impression material, used to take an impression of anatomy, which has been directly surgically exposed in the course of an operation.

A jig according to previous clauses, which once an impression has been taken of the relevant exposed anatomy, can be scanned and used to permit the co-registration of the exposed surgical anatomy to previously or intraoperatively acquired image data (e.g. CT or MRI).

A jig as described in the previous clause which is able to be returned into the same position from where the impression was first taken once, having been rapidly and appropriately modified by an associated apparatus to create cutting or drilling paths or channels.

A jig according to all previous clauses where physical fixation means can be provided at the time of molding of the registration device, to ensure, or at least increase the likelihood of, the secure placement of the tool once it is returned to the position in which the mold was taken.

A registration tool according to previous clauses with provision to interact with an associated apparatus and be accordingly modified to produce a surgical guide, jig or navigation aid.

A registration tool according to previous clauses capable of physical modification by means of a CNC process to produce a surgical drilling or cutting guide, jig, template or navigation aid.

An apparatus associated with the jig or registration tool described in previous clauses capable of carrying out the computer controlled modification of said customizable registration tool or jig.

A method and associated apparatus for the intraoperative fabrication of a surgical drilling, cutting, or positioning guide which uses a computer controlled apparatus to modify a registration tool composed of a standard component and a moldable part, modified according to a specification generated by associated software An apparatus as described in previous clauses used in combination with the jig or registration tool described in previous clauses.

An apparatus for the creation of surgical cutting or drilling guides, which combines a scanner and CNC mill or drill, such that an object can be modified to a surgical prescription for use as a surgical jig or cutting guide.

An apparatus for the creation of surgical cutting or drilling guides, which combines a scanner and CNC mill or drill, such that an object can be modified to a surgical prescription for use as a surgical jig or cutting guide within a sterile drilling chamber.

A method for the intra-operative production of a cutting or drilling guide or jig substantially as described within the accompanying description, figures, and clauses A combination cutting or drilling guide and registration device substantially as described in the accompanying description, figures, and clauses.

An apparatus for the modification of a registration device/jig substantially as described in the description, figures and clauses.

While particular elements, embodiments and applications of the present invention have been shown and described, it will be understood, that the invention is not limited thereto since modifications can be made without departing from the scope of the present disclosure, particularly in the light of the foregoing teachings.

What is claimed is:

1. A method of producing a modification plan for producing a surgical guide comprising:
   (a) obtaining a surface datum representing a configuration of a surface of an impression element providing an impression of a surgical site;
   (b) obtaining an image datum of a patient's anatomy;
   (c) obtaining surgical plan datum providing a surgical plan with respect to features in said image datum representing an anatomical feature of said patient's anatomy;
   (d) registering said impression element using said surface datum and said image data with said anatomical features of said patient's anatomy;
   (e) producing said modification plan from said surgical plan datum using the registration of said impression element with said anatomical feature, wherein said modification plan includes modifying said impression element for producing said surgical guide.

2. The method of claim 1, wherein said impression element is a molded element formed by being placed against said surgical site.

3. The method of claim 1, wherein said modification plan includes instructions for operating a production apparatus to modify said impression element.

4. The method of claim 3 further including:
   (f) registering said impression element with said production apparatus, wherein said production apparatus includes a modification tool for modifying the impression element, wherein an instruction is based on a calibrated position of said modification tool and said registration of said impression element with said production apparatus.

5. A method of producing a surgical guide comprising:
   (a) a method of producing a modification plan for producing said surgical guide, wherein said method of producing a modification plan comprises:
      (i) obtaining a surface datum representing a configuration of a surface of an impression element providing an impression of a tangible surgical site of a patient, wherein said surface datum is obtained via a surface configuration recorder;
      (ii) obtaining an image datum of said patient's anatomy;
      (iii) obtaining surgical plan datum providing a surgical plan with respect to features in said image datum representing an anatomical feature of said patient's anatomy;
      (iv) registering said impression element using said surface datum and said image data with said anatomical features of said patient's anatomy; and
      (v) producing said modification plan from said surgical plan datum using the registration of said impression element with said anatomical feature, wherein said modification plan is a plan for modifying said impression element for producing said surgical guide;
   (b) modifying said impression element in accordance with said modification plan.

6. The method of producing a surgical guide according to claim 5, wherein modifying said impression element in accordance with said modification plan includes operating a production apparatus to modify said impression element in accordance with said modification plan to produce said surgical guide.

7. The method of producing a surgical guide according to claim 5 further comprising:
   (c) placing a moldable element against said surgical site to form said impression element.

8. A production apparatus for the production of a surgical guide comprising:
   (a) a receptor assembly for receiving an impression element conforming to a shape of a tangible surgical site of a patient;
   (b) a surface configuration recorder for recording a configuration of a surface of said impression element to produce a surface datum for registering said impression element with an anatomical feature of said patient's anatomy and with said production apparatus;
   (c) a processor configured to determine patient registration data from image data of said patient's anatomy and said surface datum, wherein a registration datum of said patient provides a registration of said impression element with said anatomical feature; and
   (d) a modification tool for modifying said impression element, wherein said modification tool and said impression element are positionable in a plurality of predetermined relative positions to allow said impression element to be modified in accordance with a modification plan, wherein said modification plan is a plan for modifying said impression element and is derived from a surgical plan and a registration of said impression element with said anatomical feature of said patient's anatomy.

9. The apparatus of claim 8, wherein said modification tool includes a tool selected from the group consisting of a cutter for cutting said impression element, a drill for drilling said impression element, a milling component for milling said impression element, a slot saw for sawing, and a marker for marking said impression element.

10. The apparatus of claim 8 further comprising:
    (e) a processor for determining, from said modification plan and a registration of said apparatus with said impression element, a desired relative position of said modification tool with respect to said impression element to enable said impression element to be modified in accordance with said modification plan.

11. The apparatus of claim 8, wherein said processor is configured to obtain said modification plan from an external computing device.

12. The apparatus of claim 8, wherein said processor is configured to determine how to modify said impression element in accordance with said surgical plan by using said registration data to determine how a respective impression element will align with said tangible surgical site of said patient, and thereby determining how to modify said impression element in order to provide a configuration at said tangible surgical site of said patient that is in accordance with said surgical plan.

13. The apparatus of claim 8, wherein said processor is configured to register said impression element with said production apparatus, using said surface datum.

14. The apparatus of claim 8, wherein a processor is configured to be calibrated with a relative position of said surface configuration recorder and said modification tool.

15. The apparatus of claim 8, wherein a control unit is configured to adjust a position of said receptor assembly and said modification tool to enable modification in accordance with said modification plan.

16. The apparatus of claim 8, wherein a control unit is configured to control said modification tool to modify said impression element in accordance with said modification plan.

17. The apparatus of claim 8, wherein a control unit is calibrated with relative positions of said surface configuration recorder and of said modification tool.

18. The apparatus of claim 8, wherein said control unit is configured to obtain a spatial registration datum providing a registration of said impression element with said apparatus, and wherein said control unit is configured to control the modification tool to modify a received impression element in accordance with a modification plan using said spatial registration datum.

19. The apparatus according to claim 8, wherein said apparatus is part of a kit for producing said surgical guide, wherein said kit also comprises a moldable material for placing against said tangible surgical site of said patient to form said impression element.

20. A computer program for performing said method of claim 1 when executed on a computing device.

* * * * *